United States Patent
Namioka et al.

(10) Patent No.: US 8,060,329 B2
(45) Date of Patent: Nov. 15, 2011

(54) DISPLAY-DEVICE INSPECTION APPARATUS AND INSPECTION METHOD

(75) Inventors: Yasuo Namioka, Tokyo (JP); Akiko Kase, Yokohama (JP); Shinji Harasawa, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 761 days.

(21) Appl. No.: 11/791,755

(22) PCT Filed: Nov. 30, 2005

(86) PCT No.: PCT/JP2005/022023
§ 371 (c)(1),
(2), (4) Date: May 29, 2007

(87) PCT Pub. No.: WO2006/059662
PCT Pub. Date: Jun. 8, 2006

(65) Prior Publication Data
US 2008/0125993 A1    May 29, 2008

(30) Foreign Application Priority Data
Nov. 30, 2004  (JP) .............................. P2004-346000

(51) Int. Cl.
*G01P 21/00*  (2006.01)
(52) U.S. Cl. ........................................................ 702/94
(58) Field of Classification Search .................... 702/94; 356/237.5
See application file for complete search history.

(56) References Cited

U.S. PATENT DOCUMENTS
2005/0254045 A1 *  11/2005  Weiss et al. ................ 356/237.5

FOREIGN PATENT DOCUMENTS
| JP | 62-279475 | 12/1987 |
| JP | 6-138047 | 5/1994 |
| JP | 8-184570 | 7/1996 |
| JP | 8-327560 | 12/1996 |
| JP | 2001111987 A * | 4/2001 |

OTHER PUBLICATIONS

Ten Ikegaki et al., "Handbook for Manufacturing Technology of Liquid Crystal Display, 1st Edition," Science Forum (Apr. 20, 1992), pp. 3-9 and 349-358, with English-language translation of pp. 350-355.

* cited by examiner

*Primary Examiner* — Drew A Dunn
*Assistant Examiner* — Xiuquin Sun
(74) *Attorney, Agent, or Firm* — Finnegan, Henderson, Farabow, Garrett & Dunner, L.L.P.

(57) ABSTRACT

A display-device inspection apparatus includes a pointing device for following a position where an identification for identifying an attention area on an inspection image is displayed on the inspection image simultaneously, an attention area information extracting part for converting the identification into outline coordinate data to extract both positional information and shape information related to the attention area m a screen, an attention area information storing part for classifying and storing the positional information and the shape information on a basis of a predetermined standard of classification, and an analysis result outputting part for outputting inspection result information constructed by analyzing contents stored in the attention area information storing part.

4 Claims, 25 Drawing Sheets

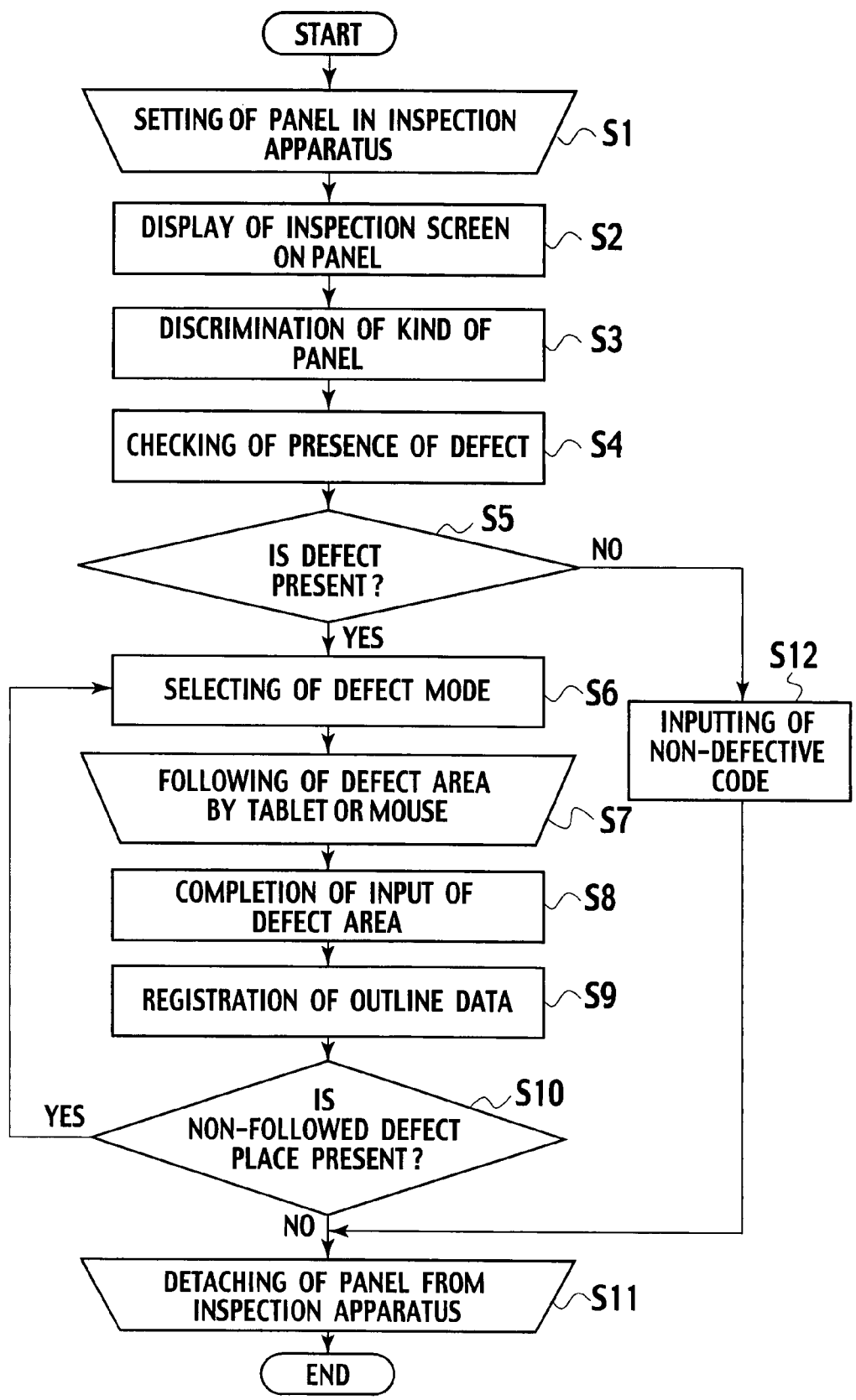

☐ STORING BY CHAIN CODES
▨ STORING BY COORDINATES

| STARTING POINT | | AREA | REPRESENTATIVE POINT | |
|---|---|---|---|---|
| #1, $x_1$ | #1, $y_1$ | (#1,$x_1$,#1,$y_1$) 01212120011······ | #1, $x_r$ | #1, $y_r$ |
| #2, $x_1$ | #2, $y_1$ | (#2,$x_1$,#2,$y_1$) 01221220011······ | #2, $x_r$ | #2, $y_r$ |
| #3, $x_1$ | #3, $y_1$ | – | #3, $x_1$ | #3, $y_1$ |

FIG. 7

| INFO. FOR SPECIFYING PANEL | DEFECT PLACE SERIAL No. | DEFECT MODE | DEFECTIVE/NON-DEFECTIVE | INSPECTING TIME |
|---|---|---|---|---|
| RAZA0371A,(B1) | #1 | UNEVENNESS | DEFECTIVE | 2004/11/20 15:01 |
| ↓ | #1 | UNEVENNESS | NON-DEFECTIVE | 2004/11/20 15:12 |
| ↓ | #2 | POINT | DEFECTIVE | 2004/11/20 15:30 |

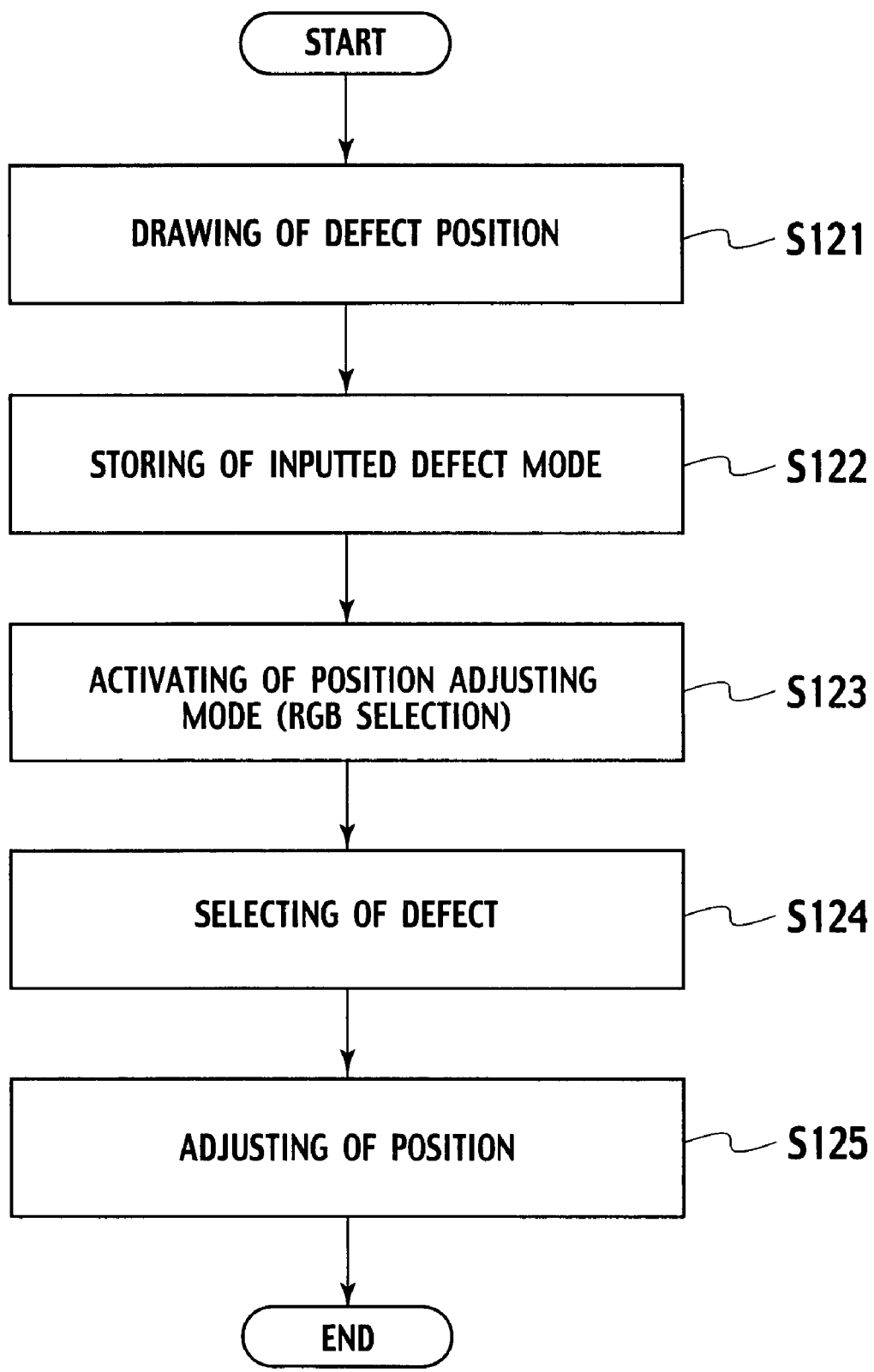

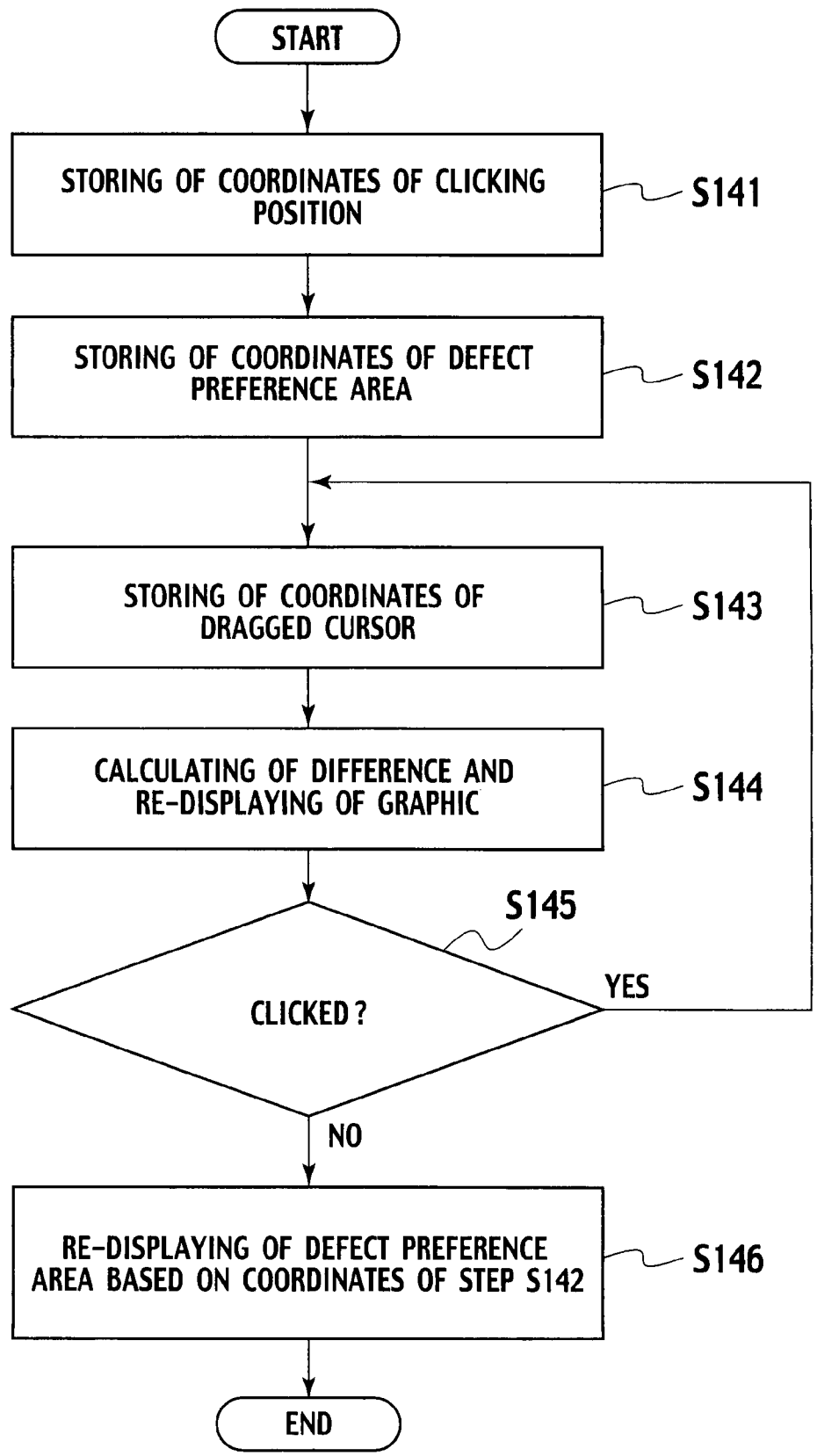

DISPLAY-DEVICE INSPECTION APPARATUS AND INSPECTION METHOD

TECHNICAL FIELD

The present invention relates to a display-device inspection apparatus and a display-device inspection method, both of which are provided to accumulate and analyze inspection results in a screen inspection of a manufacturing process of display devices.

BACKGROUND OF ART

In the manufacturing process of display devices, such as liquid crystal displays and plasma displays, conventionally, it is carried out to inspect a screen of the display device. In this screen inspection, it is performed to check the operation of manufactured display devices and confirm the presence/absence of unintended defects (point defect, line defects, etc.) on display screens.

In this screen inspection, an inspection image for inspection is displayed on each display device, while an inspection staff confirms the presence/absence of an unintended defect visually. When a display device includes an unintended defect on visual confirmation, the same display device is treated as a defective product and excluded from shipment so long as the unintended defect does not meet the quality standard for display device in terms of its position, shape, size, kind and so on (see non-patent document 1).

Non-patent Document 1: "Practical Manual for Liquid Crystal Display Manufacturing Devices" written by Ten Ikegaki and Hiroshi Wada and published by Science Forum Co. Ltd.

DISCLOSURE OF THE INVENTION

In the above-mentioned prior art screen inspection for display device, however, it is not easy to accumulate and stock respective results in the screen inspection against a number of display devices and further analyze the so-stocked results as occasion demands in spite of the possibility of confirming the presence/absence of an unintended defect.

Considering the above-mentioned problem, an object of the present invention is to provide display-device instruction apparatus and method that allow respective results of the screen inspection in the manufacturing process of display devices to be stocked for storage with ease and that further enable the stored results of the screen inspection to be analyzed or outputted as occasion demands, thereby improving both production efficiency and quality of the display devices.

The present invention is characterized by a display-device inspection apparatus for inspecting a display device on viewing an image displayed on a screen of the display device, comprising: identification position nominating means for nominating a position where an identification for identifying an attention area on the inspection image is displayed on the inspection image simultaneously; attention area information extracting means for converting the identification into image data thereby extracting both positional information and shape information related to the attention area in the screen; attention area information storing means for classifying and storing the positional information and the shape information on a basis of a predetermined standard of classification; and analysis result outputting means for outputting inspection result information constructed as a result of analyzing contents stored in the attention area information storing means.

Additionally, the present invention is characterized by display-device inspection apparatus for inspecting a display device on viewing an image displayed on a screen of the display device, comprising: attention area information extracting means that traces both shape and position of a attention area displayed on the inspection image onto a sheet overlaid thereon and converts the shape and position of the attention area traced onto the sheet into image data thereby extracting both positional information and shape information related to the attention area in the screen; attention area information storing means for classifying and storing the positional information and the shape information on a basis of a predetermined standard of classification; and analysis result outputting means for outputting inspection result information constructed as a result of analyzing contents stored in the attention area information storing means.

In these apparatus, it is preferable that the attention area information extracting means adopts a chain-code analysis for encoding an outline when converting into the image data.

Further, the present invention is characterized by a display-device inspection method of inspecting a display device on viewing an image displayed on a screen of the display device, comprising: a position nominating step of allowing identification position nominating means to nominate a position where an identification for identifying an attention area on the inspection image is displayed on the inspection image simultaneously; an extracting step of allowing attention area information extracting means to convert the identification into image data thereby extracting both positional information and shape information related to the attention area in the screen; a storing step of allowing attention area information storing means to classify and store the positional information and the shape information on a basis of a predetermined standard of classification; and an outputting step of allowing analysis result outputting means to output inspection result information constructed by analyzing contents stored in the attention area information storing means.

Still further, the present invention is characterized by a display-device inspection method of inspecting a display device on viewing an image displayed on a screen of the display device, comprising: an extracting step of tracing both shape and position of an attention area displayed on the inspection image onto a sheet overlaid thereon and converting the shape and position of the attention area traced onto the sheet into image data thereby extracting both positional information and shape information related to the attention area in the screen; a storing step of allowing attention area information storing means to classify and store the positional information and the shape information on a basis of a predetermined standard of classification; and an outputting step of allowing analysis result outputting means to output inspection result information constructed by analyzing contents stored in the attention area information storing means.

BRIEF DESCRIPTION OF THE DRAWINGS

FIG. 2 is a flow chart to explain procedures of the screen inspection of the display-device inspection apparatus in accordance with the first embodiment of the present invention.

FIG. 7 is a view showing one example of inspection data of the screen inspection result by the display-device inspection apparatus in accordance with the first embodiment of the present invention.

FIG. 12 is a flow chart to explain the addressing function of the present invention.

FIG. 14 is a flow chart to explain a shift mode function of the present invention.

BEST MODE FOR CARRYING OUT THE INVENTION

Embodiments for carrying out the present invention will be described below. Note that it is possible to handle three kinds of data structures in the present invention. That is, there are 1: data formed by a chain code as outline data; 2: data formed by a point sequence on an outline as outline data; and 3: data which is different from the data structures of the above items 1 and 2 and which is formed by an aggregation of points existing in an outline in place of the data representing the outline itself. The data structure of the item 1 is one suitable to the second embodiment mentioned later, providing outline data representing a defective spot since image data obtained by a scanner or the like is converted to chain data by a predetermined technique. Provided that an interior of the outline is divided into grids at predetermined intervals, again, the data structure of the item 3 is identical to data consisting of representative coordinate values (e.g. gravity point of each grid) of data existing in respective grids.

1$^{st}$. Embodiment

Figure 1:
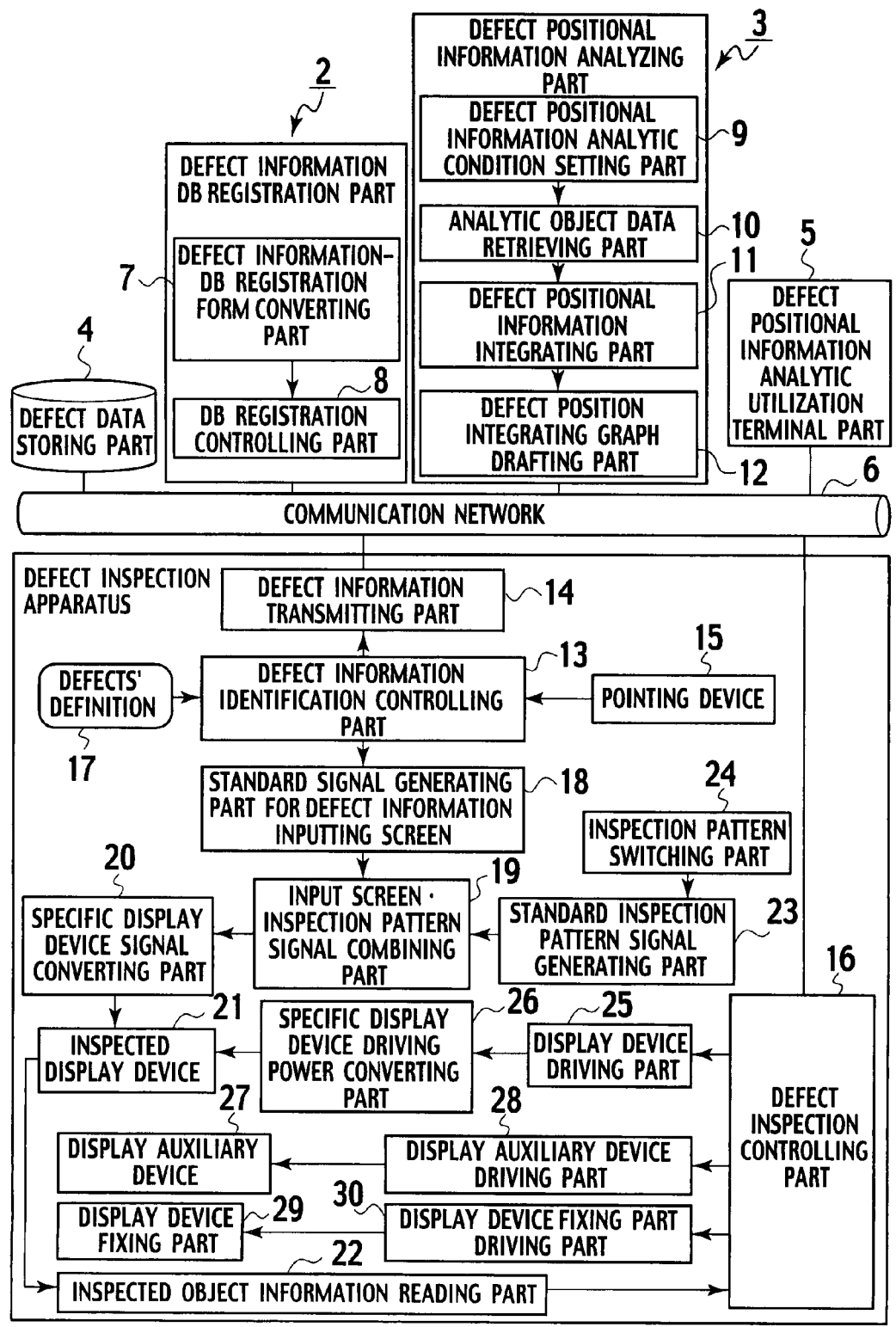
FIG. 1 is a structural view to explain a whole constitution of a display-device inspection apparatus in accordance with a first embodiment of the present invention.

FIG. 1 is a structural view to explain a whole structure of a display-device inspection apparatus in accordance with the first embodiment of the present invention.

As shown in FIG. 1, a system of the present invention generally comprises a defect inspection apparatus 1 for performing the screen inspection of display devices, a defect information DB registration part (attention area information storing means) 2 for registering defect information (defect selecting area, attention area) extracted by the screen inspection in a data base, a defect positional information analyzing part (analysis result outputting means) 3 for analyzing the defect information, a defect data storing part 4 that accumulates the defect information to form the data base on memory, a defect positional information analytic utilization terminal part 5 for analyzing and utilizing the detect information accumulated in the detect data storing part 4 and a communication network 6 formed by a communication network, for example, internet, LAN and so on.

Again, the defect information DB registration part 2 includes a defect information-DB registration form converting part 7 and a DB registration controlling part 8.

Again, the defect positional information analyzing part 3 includes a defect positional information analytic condition setting part 9, an analytic object data retrieving Part 10, a defect positional information integrating part 11 and a defect position integrating graph drafting part 12.

Further, the detect inspection apparatus 1 includes a defect inspection controlling part 16 for controlling the whole operation of the detect inspection apparatus 1, an inspected object information reading part 22 for reading out identifying information for identifying an inspected display device 21, a display device driving part 25, a specific display device driving power converting part 26, a display auxiliary device driving part 28, a display auxiliary device 27 for irradiating transmission light from a back face of the inspected display device 21 as occasion demands, a display device fixing part 29 for fixing the inspected display device 21 on a predetermined position into mutual electrical connection and a part (fixing part driving part) 30 for driving the display device fixing part for moving the position of the inspected display device 21 to the determined position.

Further, the defect inspection apparatus 1 includes a defect information identification controlling part 13, a defect information transmitting part 14, a standard signal generating part 18 for defect information inputting screen, a defects' definition 17, a pointing device (identification position nominating means) 15, an input screen•inspection pattern signal combining part 19, an inspected display device 21, a specific display device signal converting part 20, an inspection pattern switching part 24 and a standard inspection pattern signal generating part 23.

In this constitution shown in FIG. 1, on condition of connecting a display device as an object to be inspected to the defect inspection apparatus 1 and further displaying an inspection image on this display device, an inspecting staff inspects the position of a defect in the screen visually. Note that the display device is illustrated by the inspected display device 21 in FIG. 1.

Next, based on the constitution shown in FIG. 1, we describe a method of inspecting a screen of the inspected display device 21 with reference to FIG. 2.

FIG. 2 shows a flow chart to explain procedures of the screen inspection by the display-device inspection apparatus in accordance with the first embodiment of the present invention.

First, the inspected display device 21 is set on the defect inspection apparatus 1 (step 1: S1). Then, the defect inspection apparatus 1 is electrically connected to the inspected display device 21 electrically. In detail, this connection is performed for the specific display device signal converting part 20, the display device driving part 25 and the specific display device driving power converting part 26. The display device driving part 25 supplies a control signal and a power for driving the inspected display device 21, while the specific display device driving power converting part 26 performs a power supply suitable for the inspected display device 21.

Next, an inspection screen is displayed on the inspected display device (panel) 21 (step 2: S2). This inspection screen has image data produced by the standard inspection pattern signal generating part 23. The inspection screen is formed by plural kinds of patterns. These patterns are switched by an inspection pattern switching part 24 if necessary for the screen inspection. Directly connected to the inspected display device 21 is the specific display device signal converting part 20 which outputs an image display signal for the inspection screen and generates the image display signal in accordance with the kind of the inspected display device 21.

Note that the input screen•inspection pattern signal combining part 19 is disposed between the standard inspection pattern signal generating part 23 and the specific display device signal converting part 20. This input screen•inspection pattern signal combining part 19 is connected to the standard signal generating part 18 for defect information inputting screen, which is under the control of the defect information identification controlling part (attention area information extracting means) 13.

Outputted from the standard signal generating part 18 for defect information inputting screen are display signals for a mouse cursor and a function selecting menu that are to be displayed on the screen of the inspected display device 21 at the same time of displaying the inspection image (inspection patterns) on the same screen. These mouse cursor and function selecting menu are displayed on the screen of the inspected display device 21 in conjunction with a manipulation on the pointing device 15.

Next, it is executed to discriminate the kind of an inspected display device (panel) 21 (step 3: S3). This discrimination of the kind is carried out by the inspected object information reading part 22. Note that this step 3 may be carried out when the inspected display device 21 is connected to the defect inspection apparatus 1 at step 1. Alternatively, it may be accomplished since a not-shown barcode reader reads out a barcode attached to an inspected display device 21 to represent its kind, inherent information for identification and so on. Additionally, the reading part 22 may be replaced by an operator's manual inputting with the appropriate use of a user interface.

Next, it is executed to examine the presence/absence of a defect on the screen of the inspected display device 21 (step 4: S4). Hereat, with the use of an inspection image displayed on the screen of the inspected display device 21, it is carried out to examine the presence/absence of a defect visually. The inspection image displayed on the inspected display device is formed by color, pattern, brightness, etc. that facilitate discovery of a variety of defects.

As for the defects on the screen to be examined at this process, there are faulty points, for example, point due to lights-out or lack about a display dot (point defect), longitudinal streak-shaped line (line defect), color shading, irregular brightness, etc. There is a case that a plurality of faulty points forming the defects are present on the same screen simultaneously or that a combination of several kinds of faulty points are present on the screen.

Next, it is executed to judge whether the defect place is present on the screen of the inspected display device 21 or not (step 5: S5). At this judgment, if no defect place is found and the display device is a good article (No at step 5), then a non-defective code is inputted (step 12: S12). Subsequently, the inspected display device 21 is detached from the defect inspection apparatus 1 (step 11: S11) and successively, a series of inspections are completed.

On the other hand, if the defect place is discovered on the screen of the inspected display device 21 at step 5: S5 (Yes at step 5), a defect mode is selected to start an operation to acquire outline data of the defect place.

Next, with respect to the defect place whose existence has been confirmed on the screen of the inspected display device 21, the kind of defect is selected out of several kinds of defect modes established in advance, with the use of the pointing device 15 (step 6: S6).

This defect mode display is displayed on the screen of the inspected display device 21 while being superimposed on the inspection image. On the defect mode display, there are displayed several kinds of defect modes (the kinds of defects on the screen), for example, items of "Uneven", "Blue Spot", "Bright Point", "Bright Point Center", etc. A definition to display these items is previously stored in the defects' definition 17.

Corresponding to the defect mode on selection, it is executed to select an outline data extracting method for the defect place to be data-processed at the defect information identification controlling part 13.

Figure 3A:
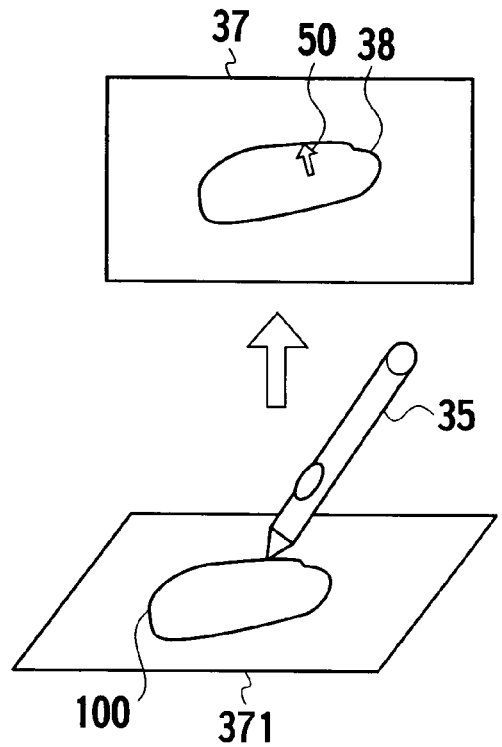
FIG. 3A is an explanatory view to explain area inputting means used for the screen inspection of the display-device inspection apparatus in accordance with the first embodiment of the present invention.
Figure 3B:
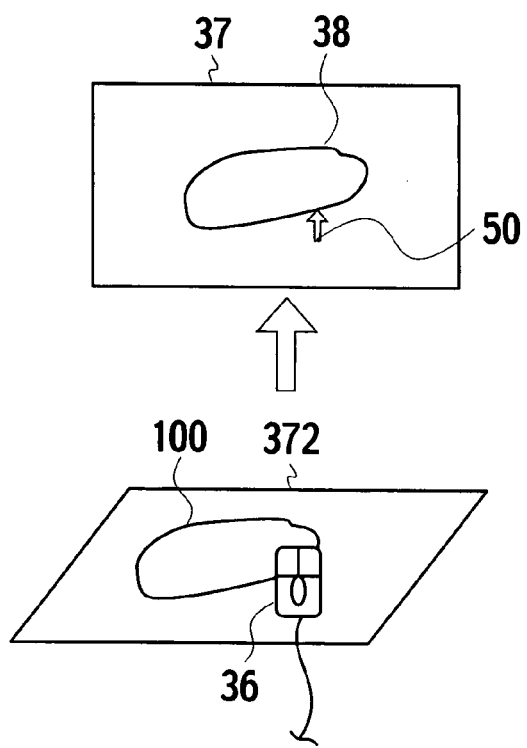
FIG. 3B is an explanatory view to explain another form of the area inputting means used for the screen inspection of the display-device inspection apparatus in accordance with the first embodiment of the present invention.

Note that the pointing device 15 for use may be embodied in forms of e.g. FIGS. 3A and 3B.

FIGS. 3A and 3B are explanatory views to explain area inputting means used in the screen inspection by the display-device inspection apparatus in accordance with the first embodiment of the present invention.

As for the pointing device 15, there are known various types of devices, as referred with FIG. 3. That is, there is available a pen-type input device 35 shown in FIG. 3A or a mouse 36 shown in FIG. 3, for the pointing device 15. Besides these devices, a not-shown digitizer etc. may be employed as the pointing device 15.

Note that FIG. 3A illustrates a condition where the pointing device 15 (the pen-type input device 35) draws a defect preference area 100 as a result of following either a defect place 38 existing on a panel screen (the inspected display device 21) 38 to be inspected or a vicinity of the defect place 38. Illustrated on the outline of the defect place 38 is a cursor 50 that represents a position of the pointing device 15. Depending on a situation of the defect place 38, there is a case that it is difficult to describe a place of the defect and its area precisely. With the aid of later-mentioned various functions, however, an inspecting staff could earmark a point defect, a line defect and a defect area having a certain extensity as precisely as possible.

The defect place 38 is described in the same shape as the track (the defect preference area) 100 that has been described since the inspection staff handled the pen-type input device 35 on a tablet 371 while looking the defect place 38 displayed on the display panel screen 37.

Additionally, FIG. 3B illustrates one example of the mouse 36 as the pointing device 15. For instance, a mouse pad 372 is mounted on a plane for manipulating the mouse 36 thereon. Thus, by following the defect preference area 100 transcribed on the mouse pad 372 by the use of the mouse 36, the defect place 38 is displayed on the display panel 37. Illustrated on the outline of the defect place 38 is the cursor 50 that represents a present position of the mouse 36.

Next, it is performed to follow the outline of a defect area (the defect preference area) forming the defect place confirmed on the screen of the inspected display device 21 with the use of the pointing device 15, such as the tablet or the mouse 36 (step 7: S7).

By following the outline of the defect place (attention area) confirmed on the screen of the inspected display device 21 by the pointing device 15, at this step, it is performed to take, as the outline coordinate data, information about the track into the defect information identification controlling part 13.

The track of the pointing device 15 following the outline of the defect area is described on the screen of the inspected display device 21. When the defect area is formed by a point, it is described in the form of a circle centering on a dotted defect place (point defect). As this displaying of the track allows both position and shape of the defect place confirmed on the screen to be identified with ease visually, the workability is also improved.

Next, the inputting of the defect area is completed (step 8: S8). For one defect area, at this step, it is performed to follow its outline by means of the pointing device 15 and the outline data (defect information) is retained by the defect information identification controlling part 1. A single outline data is produced with respect to one faulty are.

The track data produced by the pointing device 15 following the outline of the defect place is registered as the outline data (defect information) (step 9: S9). This registration of defect information is accomplished by transmitting objective defect information from the defect information identification controlling part 13 to the defect information transmitting part 14 and successively transmitting the objective defect information from the defect information transmitting part 14 to the defect information DB registration part 2 through the network 16.

In the defect information DB registration part 2, the defect information-DB registration form converting part 7 converts the format of defect information (data format) into a format suitable to register the format to the defect data accumulating part 4. The so-registered defect information is transmitted to the DB registration controlling part 8 and subjected to control for registering the information to the defect data accumulating part 4. In this way, the defect information is registered to the defect data accumulating part 4.

In connection with this registration, it is noted that the identifying information for identifying the inspected display device 21 read out by the inspected object information reading part 22 is also registered to the defect data accumulating part 4 in relationship to the corresponding defect information, simultaneously. In this registration of the identifying information, it is transmitted from the inspected object information reading part 22 through the defect information identification controlling part 13. Alternatively, it may be transmitted through the defect inspection controlling part 16.

Next, it is executed to judge whether there remains a defect place which has yet to be followed or not (step 10: S10). If it is judged that there remains a defect place which has yet to be followed (Yes at step 10), then the process returns to step 6: S6. Thereafter, the similar processes as mentioned above will be carried out. While, if there is no defect place which has yet to be followed, then the process goes to step 11: S11, so that a series of uptake processes for the defect information about the defect place are completed.

Figure 4:
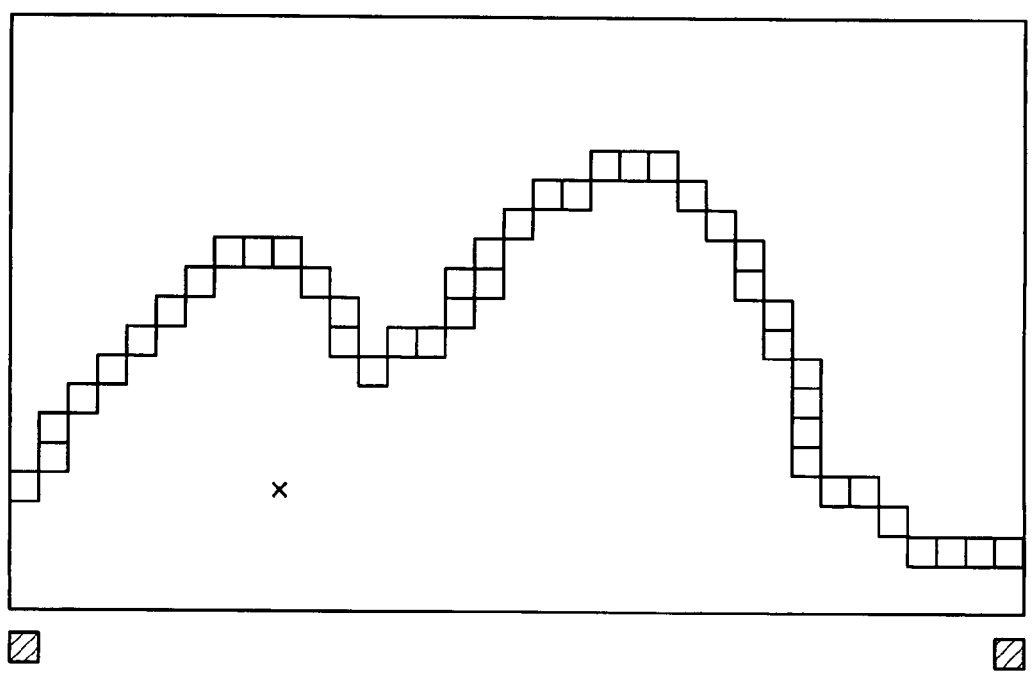
FIG. 4 is an explanatory view to explain a chain-code analysis.

FIG. 4 is an explanatory view to explain the chain code analysis by the display-device inspection apparatus, which is established mainly of the second embodiment of the present invention (Note: Mark "x" denotes a defect). As the first embodiment deals with the data structure corresponding to the above item 2, there is no need of chain code analysis. However, the so-acquired outline data may be further processed with the use of the following chain code analysis.

That is, the chain code analysis of FIG. 4 is one of methods of extracting the track data of the pointing device 15, which has been acquired by following the defect place in the previously-mentioned uptake processes for the defect information. As referred with FIG. 4, points in respective positions succeeding to a starting point are encoded in chains and stored (by outline squares in FIG. 4). While, discontinuous points are stored by coordinate values (by shaded squares in FIG. 4). In common with these chain-code data and coordinate-values data, mutually-discontinuous places are connected with each other by line segments. These line segments are stored with expressions by a linear function, various curvilinear functions and so on.

Figure 5:
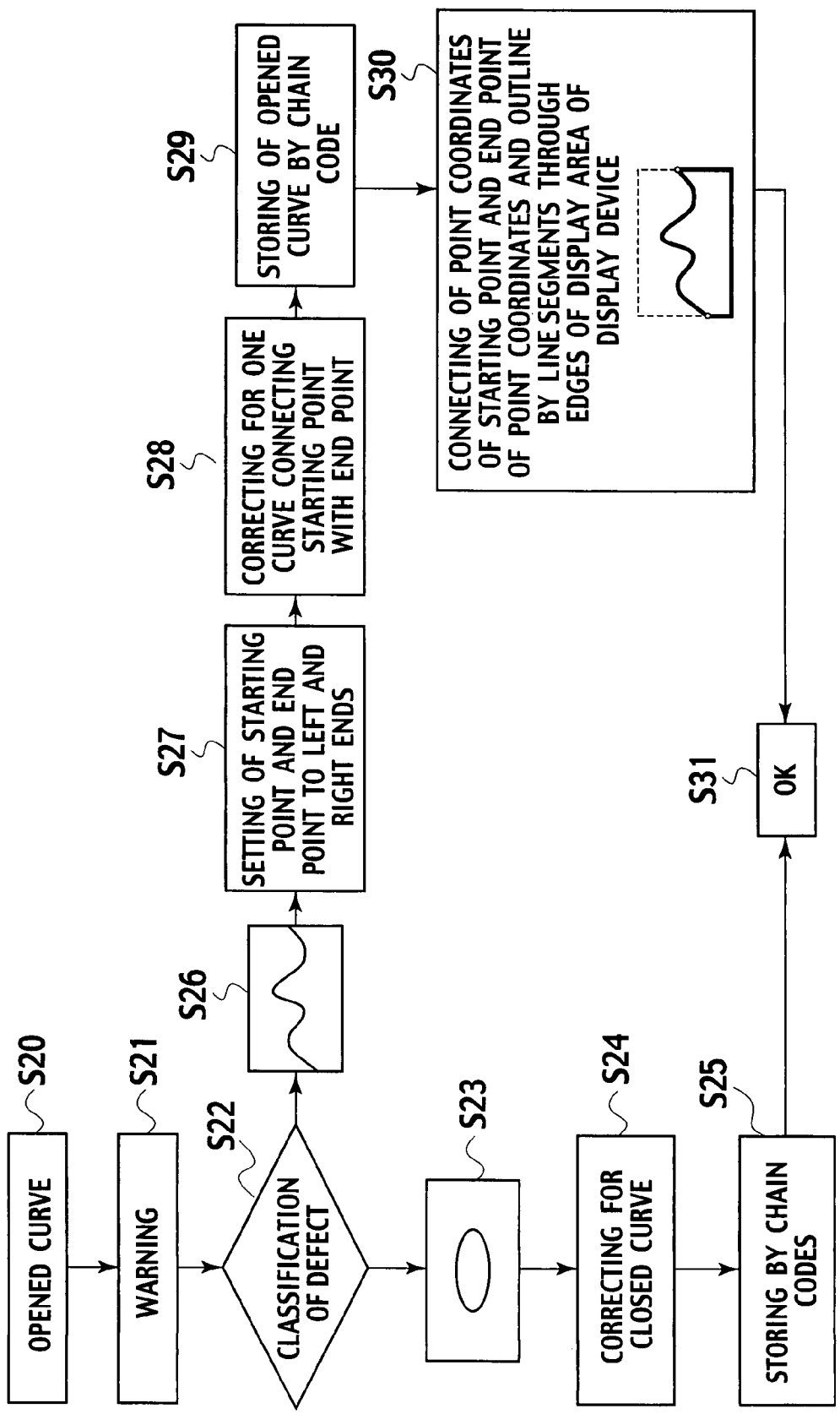
FIG. 5 is an explanatory view to explain procedures of the chain-code analysis.

FIG. 5 is an explanatory view to explain the procedures of a chain code analysis by the display-device inspection apparatus, in accordance with the second embodiment of the present invention.

As referred with FIG. 5, if the track data obtained by following the defect place is formed by an opened curve (step 20: S20), it is executed to call attention to the inspection staff by means of a display, for example, "caution" on the screen of the inspected display device 21 (step 21: S21).

Next, it is executed to judge what-like profile the track data on caution is formed (step 22: S22). With this judgment, if the profile of the track data as an object is generally formed by a closed curve (step 23: S23), the track data is corrected so as to be a proper closed curve (step 24: S24). As the closed curve is generated due to the correction, the track data is encoded in chains for storage (step 25: S25) and subsequently, a series of processes are completed (step 31: S31).

On the other hand, if the followed track data is formed by a continuous line different from a closed curve (step 26: S26), it is executed to establish a starting point and an end-point to both left and right ends of the line as an object, respectively (step 27: S27).

Next, it is executed to correct the track data so as to form one curve connecting the starting point with the end-point on establishment (step 28: S28). This operation is to correct the track of discontinuous lines produced in following the defect place. Due to this correction, the track data is reformed to be a closed curve, so that it is encoded in chains and stored (step 29: S29).

Next, as explained with reference to FIG. 4, it is executed in order to connect an independent point with the closed curve to connect point coordinates of the point with respective point coordinates of the starting point of the profile line and the end-point (step 30: S30). After this correcting process, a series of processes are completed (step 31: S31).

Figures 6A, 6B:
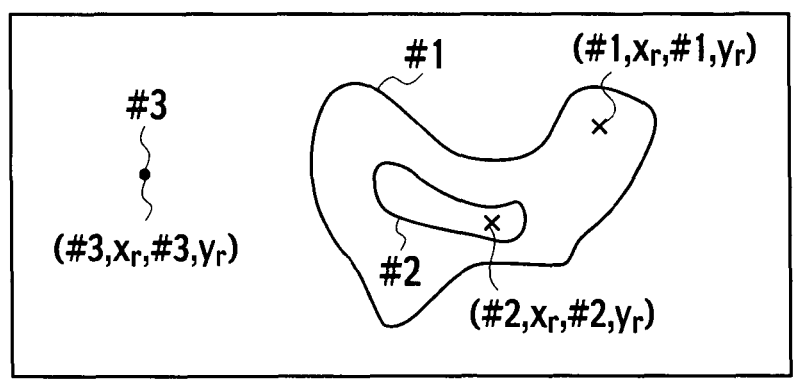
FIG. 6A is a view showing one example of inspection data of a screen inspection result by the display-device inspection apparatus in accordance with the first embodiment of the present invention.
FIG. 6B is a view showing outlines representing defective spots by the display-device inspection apparatus in accordance with the first embodiment of the present invention.

We return to the description of the first embodiment. FIGS. 6A and 6B illustrate an example of inspection data of the image inspection result by the display-device inspection apparatus in accordance with the first embodiment of the present invention.

In connection with the outline data extracted by the pointing device 15 following the detect place, FIG. 6A shows one example of data format for the outline data when it is registered in the defect data accumulating part 4. In FIG. 6B, #1, #2 and #3 denote respective defect places which have been confirmed on the screen of the inspected display device 21 and whose outlines have been followed. The defect place #1 is formed by a closed curve in which the non-defective area #2 is present. The defect place #3 is identical to a defect formed by a point (point defect).

The coordinates of the starting point are represented by "(#1, x1) (#1, y1)". Additionally, the data exhibiting an area (zone) of the defect place is encoded in chains and registered in the format of "(#1, x1) (#1, y1) 01212120011 . . . ". Additionally, "(#1, xr) (#1, yr)" is registered as a representative point. Similarly, the data for #2 and #3 is registered in the same manner. Note that the area information about #3 is not registered due to the data structure of a point.

Instead of using the chain code data, alternatively, the defect information may be stored by only coordinate data, irrespective of its continuity/discontinuity. Then, for example, the coordinate row may be expressed in the format of "(#1, x1, #1, y1) (#1, x2, #1, y2) . . . .

FIG. 7 shows one example of inspection data of the image inspection result by the display-device inspection apparatus in accordance with the first embodiment of the present invention.

The inspection data presented here is one example of format that allows the inspection staff to grasp the defect place confirmed at the inspection process for the inspected display device 21. Here, information to specify a panel for the individuality-recognizing information of the inspected display device 21 is described as "RAEA0371A, (B1)" and the serial numbers "#1" and "#2" are allocated to several defect places confirmed on the so-specified panel, respectively.

Note that the presence of two places represented by "#1" represents a ring-shaped defect area (defect selection area) where one defect area is provided, inside thereof, with another defect area. The reason of adopting this expression is that when the inspection staff finds a ring-shaped defect area at the inspection process, an understanding of such a defect as a ring-shaped defect area on the whole in spite of the presence of a normal area inside the ring would facilitate a staff's recognition about the defect area. In terms of the item of "Faulty Place Serial No.", accordingly, the ring-shaped defect area and the inside normal area are categorized by "#1" together.

The column of "Defect Mode" represents respective results obtained by classifying the states of so-confirmed defect places on the ground of defect definitions registered in the defects' definition 17 in advance. For instance, since the "defect mode" of "#1" at "Defect Place Serial No." is identical to picture unevenness, it is expressed by "unevenness". The column of "Defective/Non-defective" represents whether an individual part forming the faulty place is a non-defective one or not. For instance, since the area inside the ring-shaped defect area is a normal area, the same part is expressed by "non-defective". From a view of the ring-shaped defect area on the whole, however, the inside area is nothing but a constituent of one faulty place. The column of "Inspecting Time" represents each date and hour when the defect place was inspected.

Figure 8:
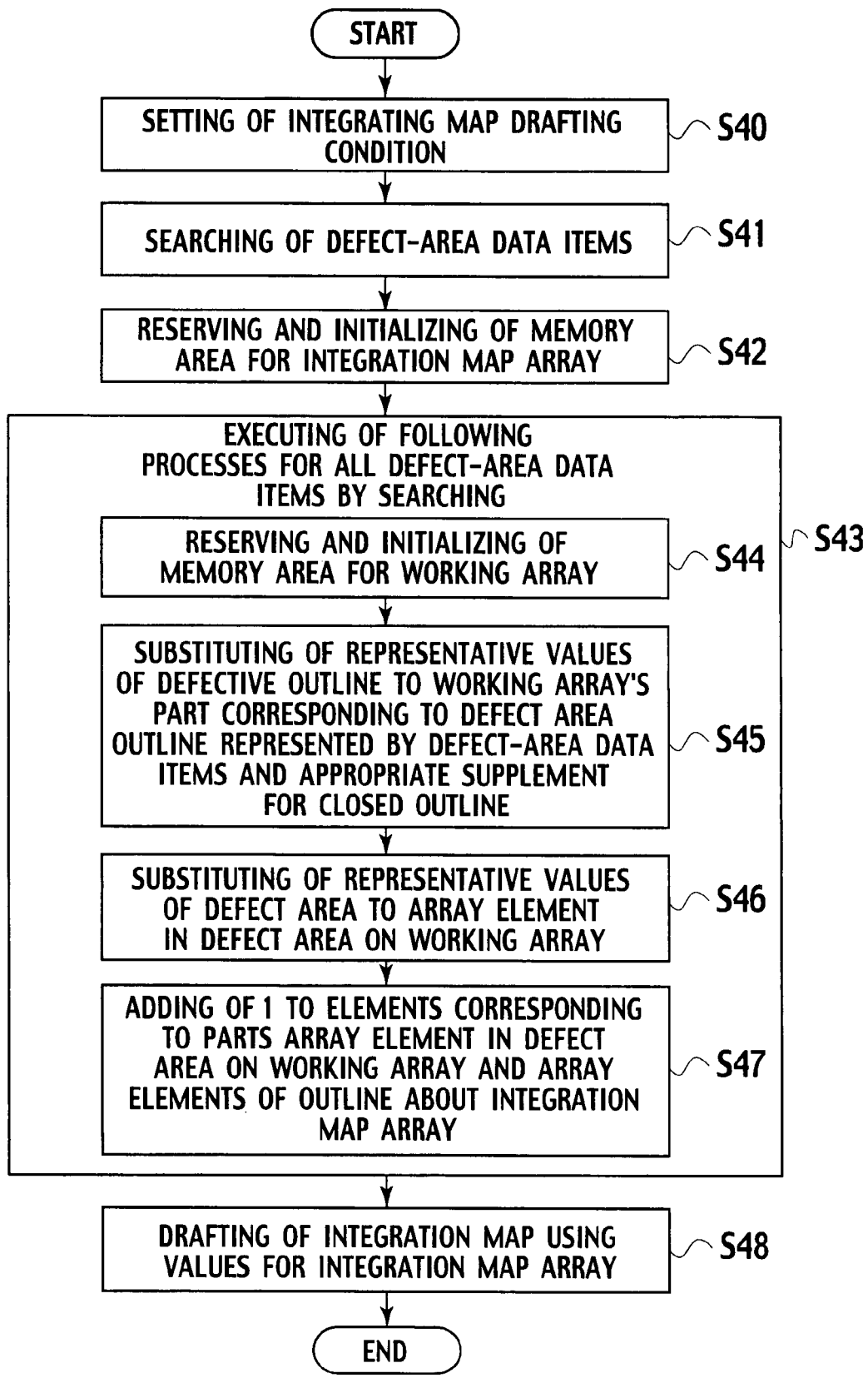
FIG. 8 is a flow chart to explain an analysis outputting process of screen inspection data by the display-device inspection apparatus in accordance with the first embodiment of the present invention.

FIG. 8 is a flow chart to explain an analysis outputting process of image inspection data by the display-device inspection apparatus in accordance with the first embodiment of the present invention.

The flow chart shown in FIG. 8 relates to one example of the analysis outputting process to analyze the defect information registered in the defect data storing part 4 with the use of the defect positional information analytic utilization terminal part 5 and further output an analytic result to the defect positional information analytic utilization terminal part 5.

Based on an input condition from the defect positional information analytic utilization terminal part 5, it is firstly executed to set an integrating map drafting condition by the defect positional information analytic condition setting part 9 (step 40: S40). Based on the integrating map drafting condition established here, it is executed to search defect-area data items against the defect information registered in the defect data storing part 4 by the analytic object data retrieving part 10 (step 41: S41).

Next, the defect positional information integrating part 11 reserves a memory area for integration map array and performs an initialization of the memory area (step 42: S42).

Next, it is executed to perform a series of processes at the following steps 44: S44 to 47: S47 with respect to all of defect-area data items obtained by the searching (step 43: S43).

First, at step 44: S44, it is executed to reserve and initialize a memory area for working array. Next, at step 45: S45, it is executed to substitute representative values of a defect outline into working array's parts corresponding to the defect area outline represented by the defect-area data items. Then, an appropriate supplement is carried out so as to close the outline. Next, at step 46: S46, it is executed to substitute values representing the defect area into elements on the working array in the defect area. Next, at step 47: S47, it is executed to add 1 to elements corresponding to array elements on the working array in the defect area and array elements of the outline.

Since these defect-area data items are not necessarily constructed by adjacent elements, they have to be supplemented for a continuous closed curve. In this view, when the data is supplemented in a manner that all elements representing the outline lie side-by-side with each other on a two-dimensional array due to the processes at a series of steps 44: S44~47: S47, there can be obtained a defect area composed of a closed curve.

Next, after a series of processes at step 43: S43 are applied to all of defect areas, the defect position integrating graph drafting part 12 drafts an integration map with the use of values for the integration map array (step 48: S48).

The so-drafted integration map is transmitted to the defect positional information analytic utilization terminal part 5 via the network 6, outputting the analysis result as the integration map.

2nd. Embodiment

Figure 9:
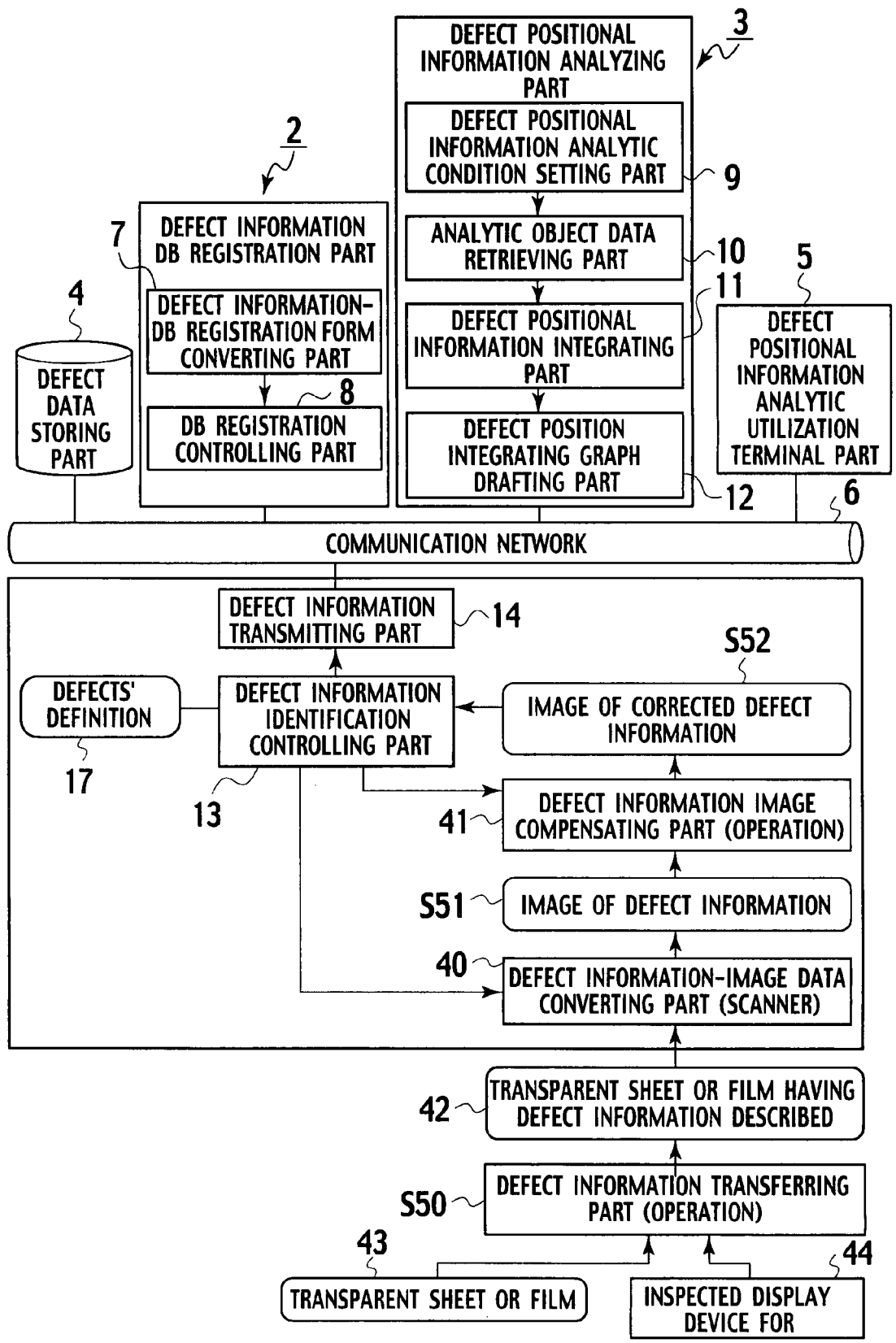
FIG. 9 is a structural view to explain a whole constitution of a display-device inspection apparatus in accordance with a second embodiment of the present invention.

FIG. 9 is a structural view to explain the whole constitution of the display-device inspection apparatus in accordance with a second embodiment of the present invention.

In the first embodiment of the present invention mentioned previously, the inspected display device 21 displays an inspection image, while the pointing device 15 follows a defect place confirmed on the inspection image. Further, the resulting track data is processed as the outline information and subsequently registered, as the defect information, into the defect data registering part 4.

On the contrary, according to the second embodiment of the present invention, there is visually confirmed a defect place on the inspection image displayed on an inspected display device 44 (the inspected display device 21). Then the so-confirmed defect place is duplicated onto a transparent sheet 43, such as OHC sheet which is overlaid on the screen of the inspected display device 44, with the use of a writing material or the like.

A defect information collecting device in accordance with the second embodiment of the present invention includes a defect information-image data converting part 40 formed by an image scanner or the like, a "defect information" image correcting part 41 for correcting the outline data of the imported defect place, the defect information identification controlling part 13, the defect information transmitting part 14 and the defects' definition 17

In the so-constructed defect information collecting device, an inspection image is displayed on the inspected display device 44, while an inspecting staff superimposes the transparent sheet 43 on the displayed screen and marks defect places that the inspection staff can ascertain through the transparent sheet 42, with the use of a writing material (color marker) or the like. As for a method of marking a punctuate defect place, the inspecting staff may either mark with a dot on the defect place or draw a line surrounding the defect place. As for a defect which is visible without the inspection image for duplicating, it is not necessarily required to display the inspection image.

For such an area as typified by picture unevenness, additionally, the staff draws a line by following the outline of the area by means of a writing material. For a linear defect place, the staff draws a line superimposed on the linear defect place. In this way, a defect information transferring operation (step 50: S50) is carried out on the transparent sheet 43. As a result of the defect information transferring operation, a transparent sheet (film) 42 having the defect information described thereon is produced.

Figure 10:
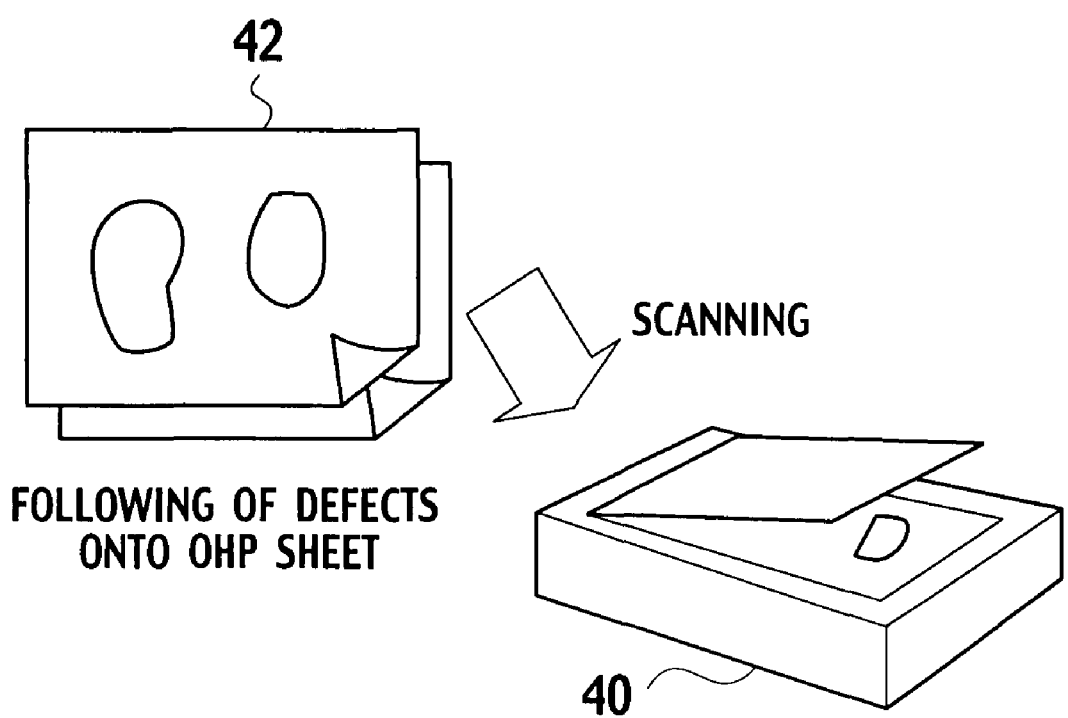
FIG. 10 is an explanatory view to explain an image-data acquisition by the display-device inspection apparatus in accordance with the second embodiment of the present invention.

Next, the defect information-image data converting part 40 converts the defect information described on the transparent sheet 42 into image data for readout. In this reading process, as referred with FIG. 10, the defect information-image data converting part 40, such as image scanner, scans the transparent sheet 42 describing the defect information produced by following it (defective panel) on the transparent sheet, such as OHP sheet, so that an image (image data) for the defect information is produced (step 51: S51).

Next, the image of defect information is compensated by the "defect Information" image compensating part 41. The compensation executed here is to make a closed curve previously mentioned with reference to FIGS. 4 and 5. By way of the compensating operation, the compensated image of defect information is produced (step S52: S52).

The produced image of defect information is transmitted to the defect information identification controlling part 13, further transmitted to the defect information DB registration part 2 through the defect information transmitting part 14 and the communication network 6 and registered in the defect data storing part 4. Note that the defects' definition 17 previously memorizes the defect information for classifying the kind of a defect with respect to the compensated image of defect information and grants a defect definition for classifying the produced image of defect information from the defects' information on memory. Note that the second embodiment adopts the chain code analysis for encoding in chains for explanation. Instead, there may be adopted an existing image processing method, for instance, method of acquiring the coordinate data as polygon data.

According to the present invention mentioned above, it is possible to provide display-device instruction apparatus and method that allow results of the screen inspection in the manufacturing process for display devices to be stocked for storage with ease and that further enable the stored result of screen inspection to be analyzed or outputted as occasion demands, thereby improving both production efficiency and quality of the display devices.

Note, without being limited to SED, liquid crystal, plasma display, Braun tube, etc., the present invention may be applicable to any display device equipped with signal inputting means for displaying an image for inspection.

<Edit Function>

The inspection apparatus of the present invention may be equipped with a function to input the position of a defect place more precisely and a function to facilitate the detecting process, both of which are mentioned below. That is, the apparatus of the present invention may include the following function at the detection of the defect area at step 7: S7 of FIG. 2 furthermore.

[Addressing Function]

The addressing function is a mode suitable for plotting the position of a point defect precisely. For instance, under condition that one of a huge amount of pixels forming the inspected display device or one of sub-pixels forming one pixel is defective, the addressing function is preferable in shifting a cross cursor onto such a defective pixel (defective sub-pixel). Of course, the same function is also preferable in manipulations shown in FIGS. 3A and 3B.

Referring to FIGS. 11A, 11B, 12 and 13, respective steps of the addressing function will be described below.

Figure 11A:
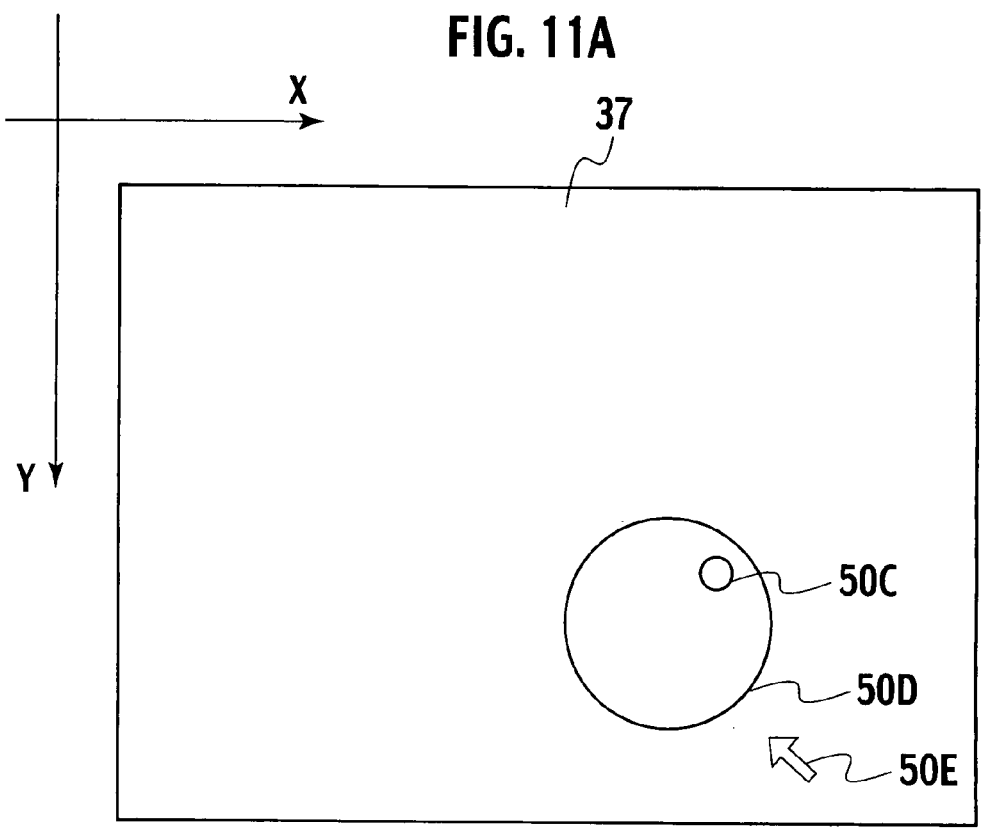
FIG. 11A is an explanatory view to explain an addressing function of the present invention.

FIG. 11A shows one displaying form of the inspection screen. By manipulating a cursor 50E on the screen (e.g. clicking) while superposing it on an area 50D representing the general position of a defect, the display is shifted to a screen of FIG. 11B.

Figure 11B:
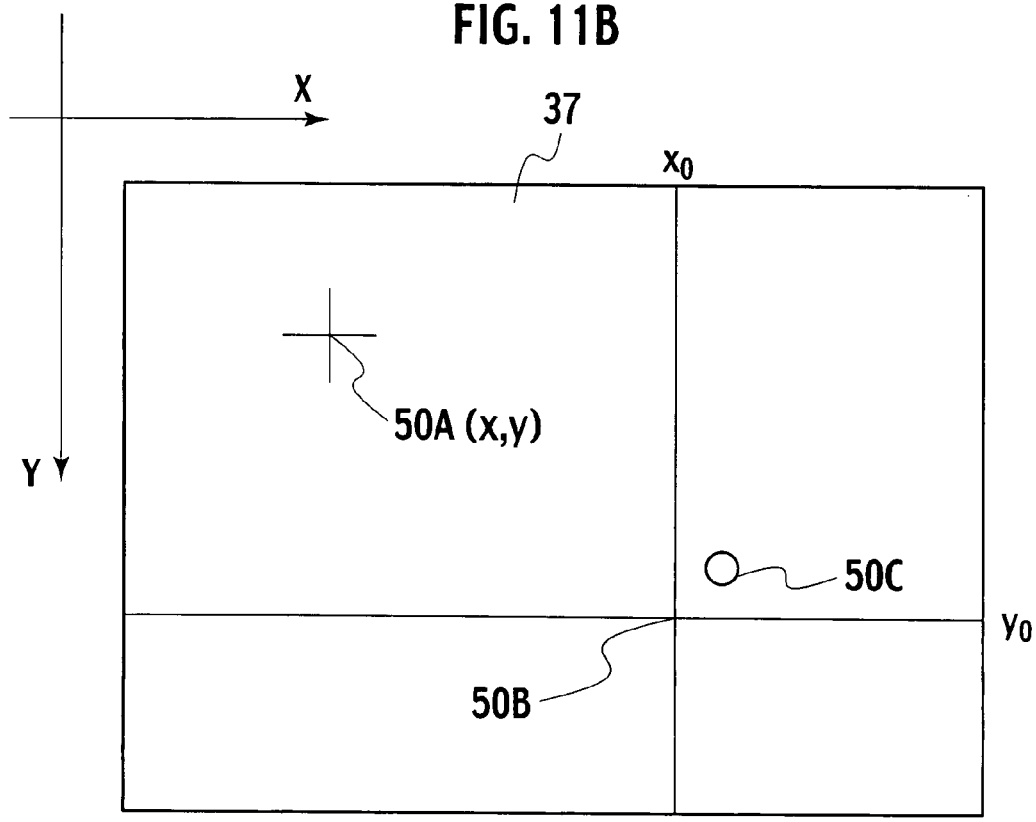
FIG. 11B is an explanatory view to explain the addressing function of the present invention, showing a screen after performing a designated operation in FIG. 11A.

In FIG. 11B, there are respectively illustrated a cursor 50A and a cross cursor 50B (Note that the position of the cross cursor 50B coincides with a center of the area 50D.) on the display panel (the inspected display device) 37. Additionally, a physical defect is present on the panel, for example, as represented by a defect 50C. As shown in FIG. 12, it is executed to draw the defect position (step 121: S121) and successively, the defect mode is inputted (step 122: S122). Here, the position adjusting mode is selected by the inspection staff. In case of moving the cursor to the point defect of a sub-pixel, it is executed to select which of sub-pixels (R), (G) and (B) should be displayed as occasion demands (step: S123) and further select a defect (step 124: S124). It is similar to step 7: S7 of FIG. 2 so far. Next, an adjusting process of the position of the defect (point defect) essential to the addressing function is performed (step 125: S125).

Figure 13A:
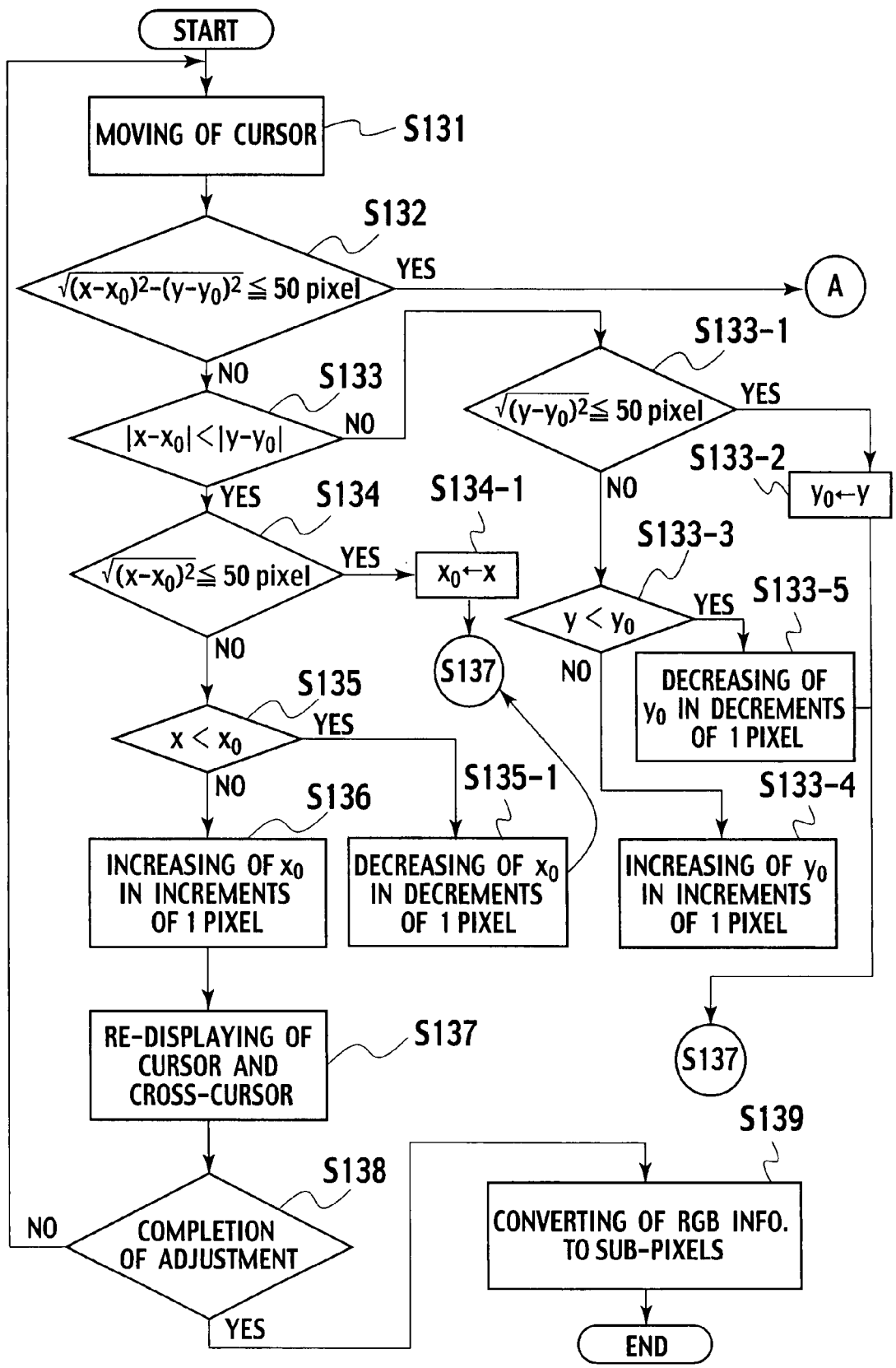
FIG. 13A is a flow chart to explain a position adjusting process of the addressing function of the present invention.
Figure 13B:
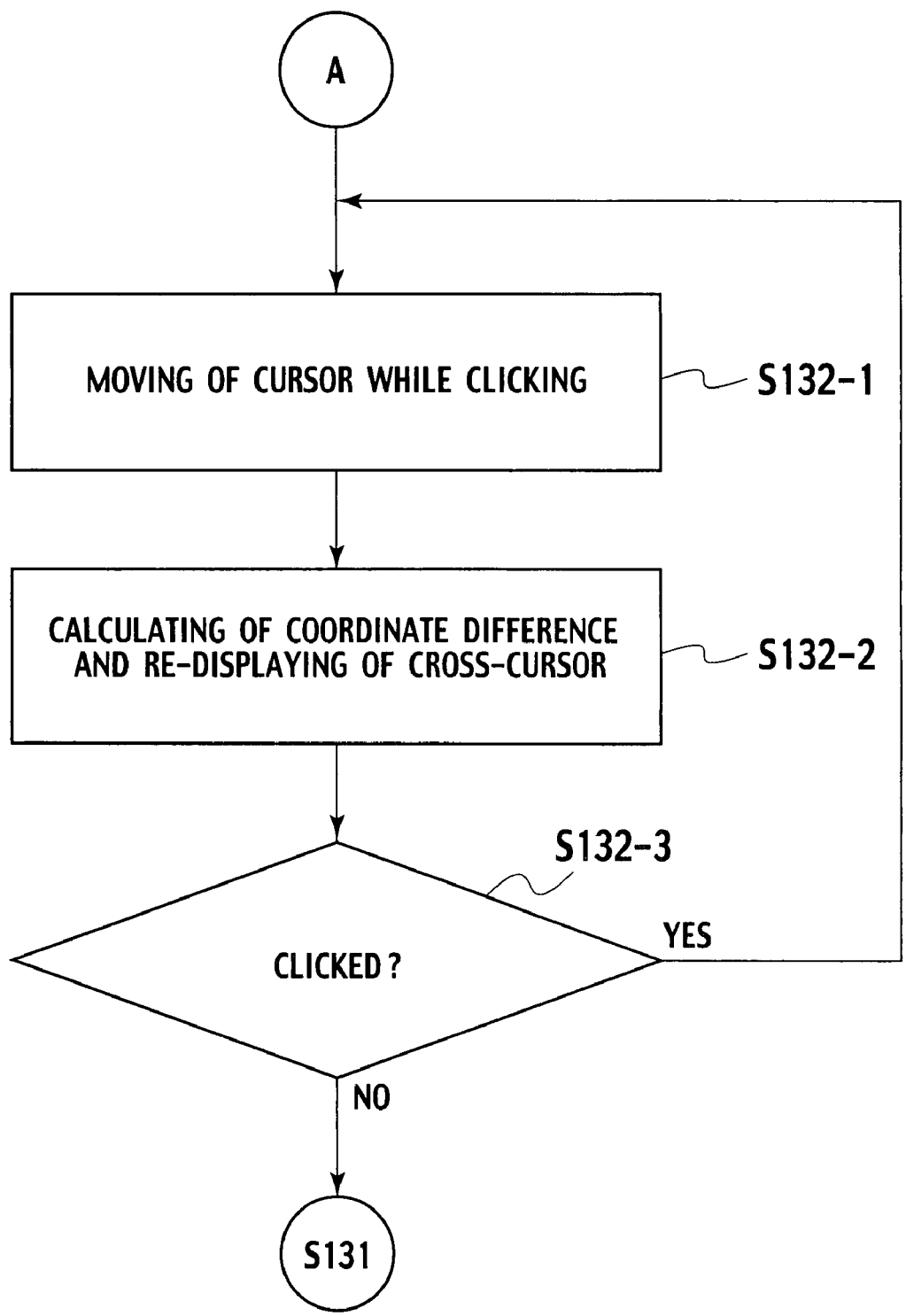
FIG. 13B is a flow chart to explain a position adjusting process of the addressing function of the present invention.

Referring to FIGS. 13A and 13B, the adjusting process will be described in detail, below.

First, when moving the cursor in order to alter the defect position (defect selecting area) selected (drawn) by step 124: S124, the positional adjustment is started (step 131, S131). Note that if the inspection staff uses e.g. a mouse for drawing, then an operation required to start the positional adjustment would be accomplished by the staff's clicking of the mouse. Alternatively, if using a tablet, the operation would be accomplished by a contact of a pen with the tablet.

Next, it is executed to judge whether a distance between the cursor 50A and the cross cursor 50B is less than a predetermined number of pixels or not (step 132: S132). In the example shown in FIG. 13A, the predetermined number of pixels is set to 50 pixels. Nevertheless, the predetermined number may be altered corresponding to required inspection accuracy, type of display devices to be inspected and so on.

At step 132: S132, if the distance between the cursor 50A and the cross cursor 50B exceeds the predetermined value (NO at step 132: S132), then it is executed to judge a magnitude relation between a distance in the direction of X-axis forming the cursor 50A and the cross cursor 50B and another distance in the direction of Y-axis forming these cursors (step 133: S133). Here, if the distance in the direction of X-axis is less than the distance in the direction of Y-axis (YES at step 133: S133), then it is executed to judge whether the distance in the direction of X-axis is less than the predetermined value or not (step 134: S134). In addition, although a predetermined value at step 133: S134 of FIG. 13A is also set to 50 pixels, the same value is alterable accordingly.

Further, at step 134: S134, if the distance in the direction of X-axis exceeds the predetermined value (NO at step 134: S134), it is executed to compare an x-component of the cursor 50A with an x-component of the cross cursor 50B (step: S135). At step 135: S135, if an x-component x of the cursor 50A exceeds an x-component $x_0$ of the cross cursor 50B (NO at step 135: S135), that is, in case of $x > x_0$, the x-component $x_0$ of the cross cursor 50B is increased in increments of 1 pixel (step 136: S136) and the cursor 50A and the cross cursor 50B are displayed again (step 137: S137). Subsequently, it is executed to judge the possibility of a completion of adjustment by means of displaying a screen (not shown) for sending inquiries to the inspection staff about the completion of adjustment (step 138: S138). When the completion of adjustment is selected at step S138 (YES at step 138: S138), the adjustment process is completed on a conversion from the information of R, G and B to sub-pixels (step 139: S139) as occasion demands. While, if the adjustment is not completed, the process is returned to step 131: S131 again.

As shown in FIG. 13B, if the distance between the cursor 50A and the cross cursor 50B is less than the predetermined value at step 132: s132 (YES at step 132: S132), the inspection staff moves the cursor 50A while maintaining a click (step 132-1: S132-1). Next, it is executed to calculate a difference between the coordinates of the cursor 50A at step 132: S132 and the coordinates of the cursor 50A at step S132-1, further calculate new coordinates of the cross cursor 50B by subtracting the above calculation result from the coordinates of the cross cursor 50 B at step S132 and display the cross cursor 50B on the new coordinates again (step: S132-2). Then, it is executed to judge whether the inspection staff still continues to click or not (step: S132-3). If the staff continues to click, then the process goes to step S132-1. While, if the staff does not continue to click, the process goes to step S132

If the judgment at step 133: S133 is NO, then it is executed to judge whether a distance in the y-component between the cursor 50A and the cross cursor 50B is less than a predetermined value (e.g. 50 pixels) or not (step 133-1: S133-1). Here, if the distance in the y-component is less than the predetermined value (YES at step 133-1: S133-1), a value in the y-component of the cursor 50A is substituted into the y-component $y_0$ of the cross cursor 50B (step 133-2: S133-2). On completion of step 133-2: S133-2, the process goes to step S137 where the cursor 50A and the cross cursor 50B are respectively displayed on new coordinates and thereafter, the above processes at steps S138 and S139 are performed accordingly.

While, at step 133-1: S133-1, if a distance in the direction of Y-axis between the cursor 50A and the cross cursor 50B exceeds the predetermined value (NO at step 133-1: S133-1), it is executed to compare the y-component of the cursor 50A with the y-component of the cross cursor 50B (step 133-3: S133-3). At step 133-3: S133-3, if a y-component of the cursor 50A is less than a y-component $y_o$ of the cross cursor 50B, that is, in case of $y < y_o$ (YES at step 133-3: S133-3), the y-component yo of the cross cursor 50B is decreased in decrements of 1 pixel (step 133-5: Si33-5). On the other hand, if the y-component of the cursor 50A is more than the y-component yo of the cross cursor 50B (NO at step S133-3), the y-component y4) of the cross cursor 50B is increased in increments of I pixel (step 133-4: S 133-4). After completing step 133-4: S133-4 or step 133-5: S133-5, the process goes to step 137: S137 where the cursor 50A and the cross cursor 50B are respectively displayed on new coordinates and thereafter, the above processes at steps S138 and S139 are performed accordingly.

At step 134: S134, if the distance in the direction of X-axis between the cursor 50A and the cross cursor 50*b* is less than the predetermined value (YES at step 134: S134), a value in the x-coordinate of the cursor 50A is substituted into the x-component $x_0$ of the cross cursor 50B (step 134-1: S134-1). On completion of step 134-1: S134-1, the process goes to step S137 where the cursor 50A and the cross cursor 50B are respectively displayed on new coordinates and thereafter, the above processes at steps S138 and S139 are performed accordingly.

If the relationship of $x < x_0$ is established at step 135 (YES at step 135: S135), a value of the x-coordinate $x_0$ of the cross cursor 50B is decreased in decrements of 1 pixel (step 135-1: S135-1). On completion of step 135-1: S135-1, the process goes to step S137 where the cursor 50A and the cross cursor 50B are respectively displayed on new coordinates and thereafter, the above processes at steps S138 and S139 are performed accordingly.

[Shift Mode Function]

Next, we explain the shift mode function with reference to FIG. 14.

The shift mode is suitable in either confirming whether the position specified by the above addressing function fairly coincides with a defect position or performing to confirm the defect position.

When calling for the shift mode function, it is executed to store coordinate values inputted by the inspection staff's clicking with the use of a mouse or a tablet pen (step 141: S141) and successively, the coordinates of a graphic representing the position and profile of a defect are stored (step 142: S142). Here, the inspection staff moves a cursor with clicking (drags a cursor), while the coordinates of the cursor are stored sequentially (step 143: S143). Next, it is executed to calculate a difference between the coordinates of the cursor at step 141: S141 and the coordinates of the cursor at step 143: S143 and also executed to move the graphic (defect selection area) representing the position and profile of the defect and subsequently, the screen is displayed again (step 144: S144). Next, it is executed to judge whether the inspection staff has made a click or not (step 145: S145). If the inspection staff keeps on clicking, the process goes to step 143: S143 (YES at step 145: S145). While, if the inspection staff does not male a click (NO at step 145: S145), the graphic (defect selection area) representing the position and profile of the defect is displayed with the coordinates at step S142 again (step 146: S146) and the process is ended. With the utilization of the shift mode function, it is possible to confirm whether the temporarily-designated position accords with the detect position precisely or not.

[Move Function]

Figure 15:
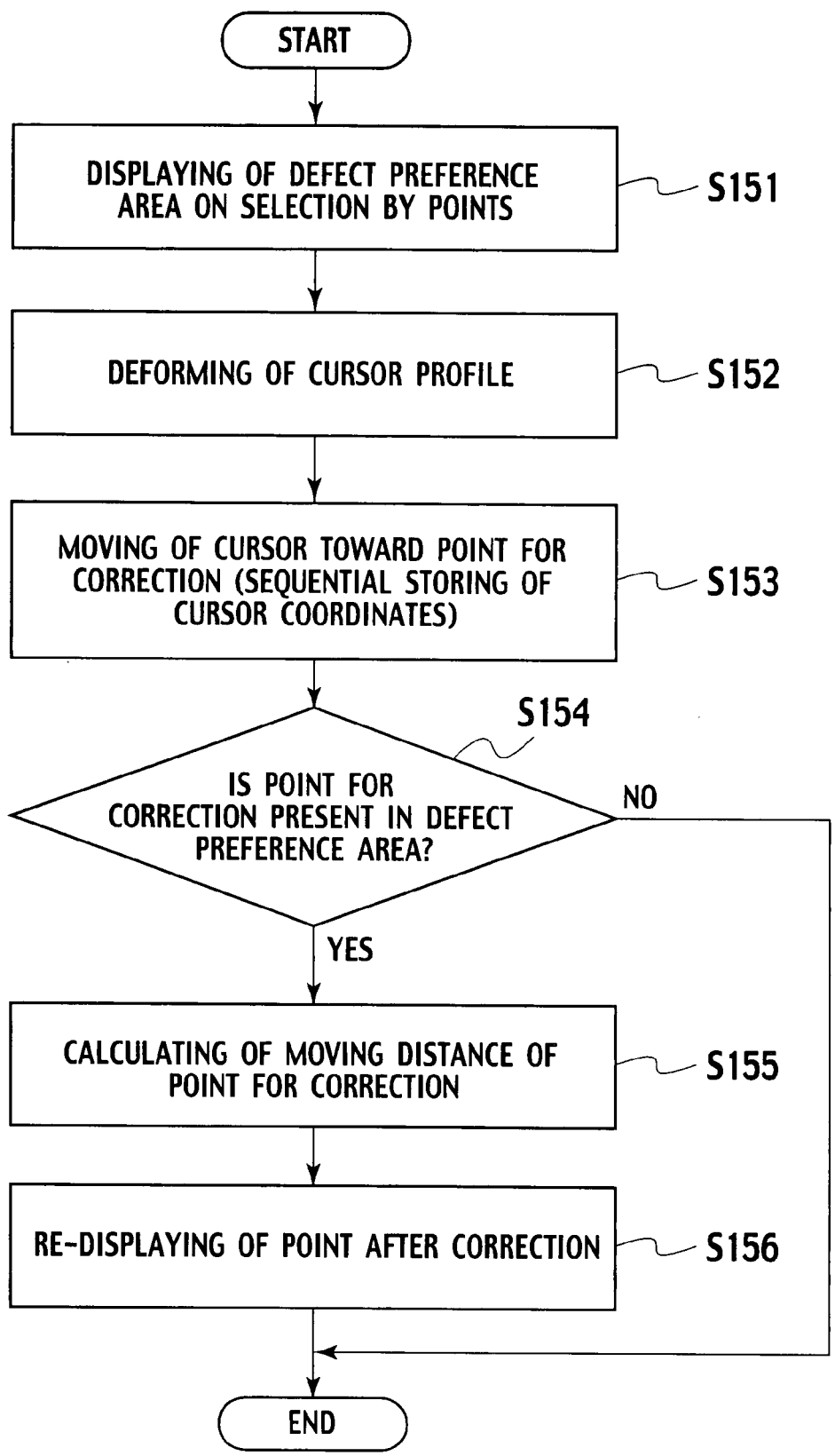
FIG. 15 is a flow chart to explain a move function of the present invention.
Figure 16A:
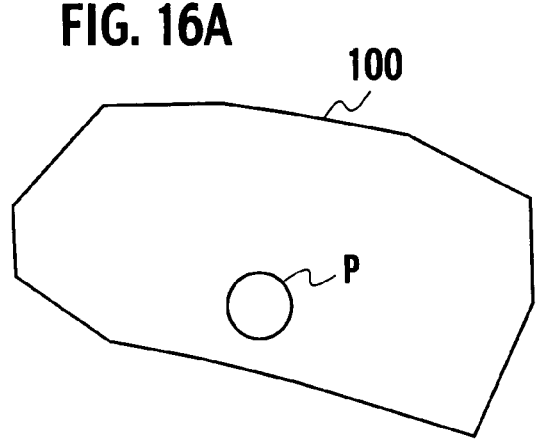
FIG. 16A is a first explanatory view to explain the move function.
Figure 16B:
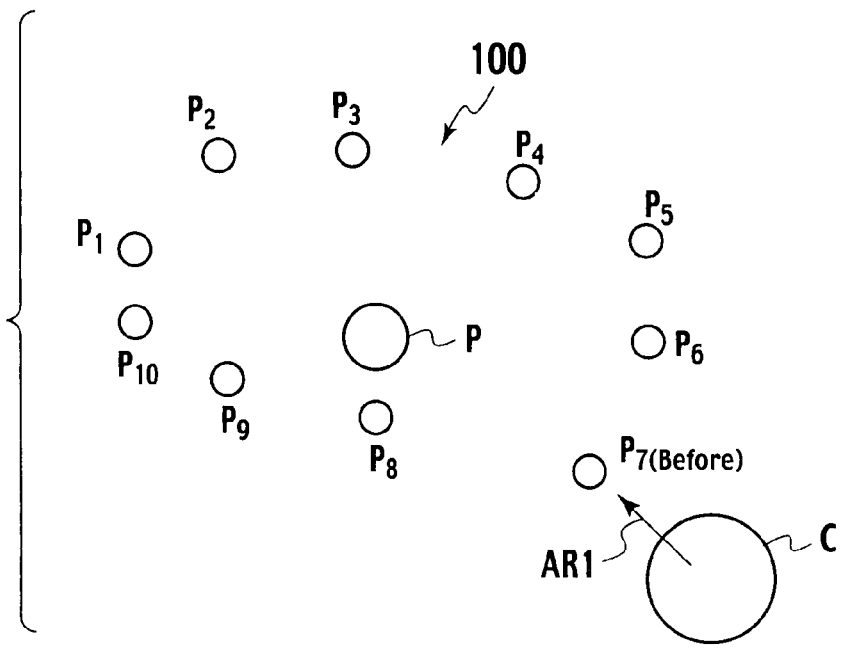
FIG. 16B is a second explanatory view to explain the move function, showing a defect selecting area before performing the move function.
Figure 16C:
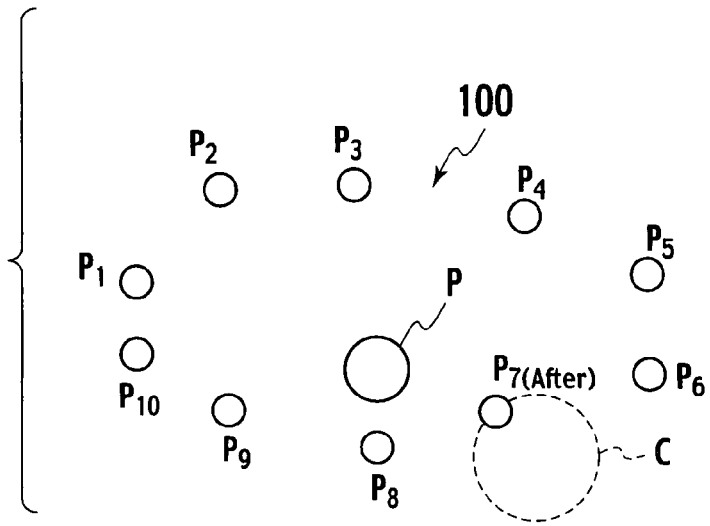
FIG. 16C is a third explanatory view to explain the move function, showing the defect selecting area after performing the move function.
Figure 17:
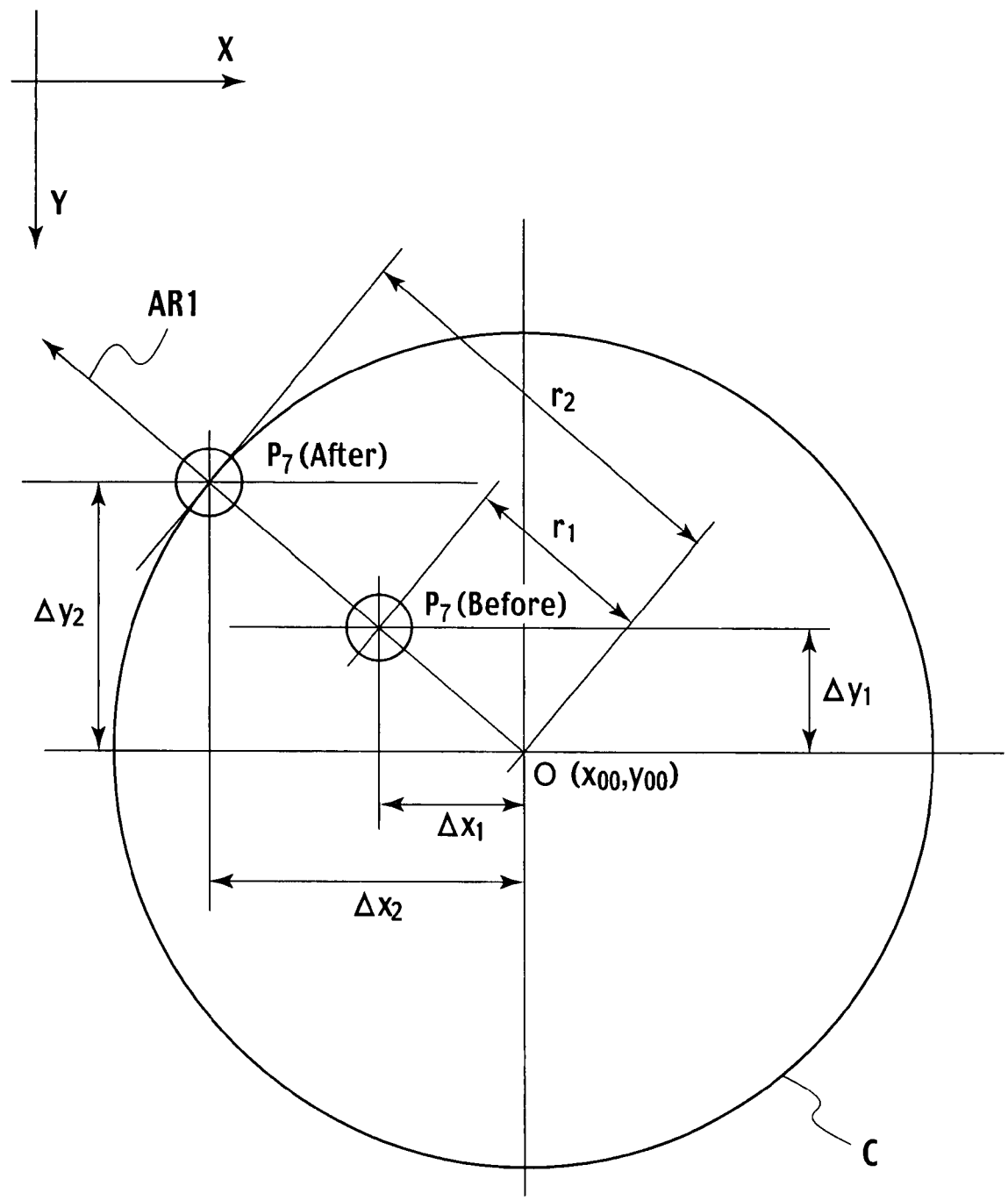
FIG. 17 is a fourth explanatory view to explain the move function.

Referring to FIGS. 15 to 17, the move function will be explained below.

In correcting the defect preference area 100 after encircling it with the use of a mouse or a tablet pen, the later-mentioned move function enables an area encircled by mistake to be corrected.

Assume in the following explanation that a graphic (defect preference area) representing the defect has been previously encircled (described) by an inspection staff in a certain process, for example, at step 7: S7 of FIG. 2.

In case of a plurality of defect preference areas, when the inspection staff selects a defect preference area to be corrected with the use of the move function, the defect represented by either a polygon or an approximated curve is re-displayed by means of points only (step: S151, FIGS. 16A and 16B).

Regarding one example shown in FIGS. 16A and 16B, it is assumed that the defect preference area 100 is displayed in the form of a polygon in order to designate a defect P (FIG. 16A). Then, when the process at step 151: S151 is executed, the defect preference area 100 is re-displayed by points $P_1$ to $P_{10}$ (FIG. 16B).

Next, a cursor C $(x_{00}, y_{00})$ on the screen is deformed to have a designated profile (step 152: S152). Note that FIG. 16B shows a situation where the cursor C is deformed to a circle having a radius $r_2$. However, the cursor C may be deformed to have any appropriate profile, for example, square and oval.

Next, the inspection staff moves the so-deformed cursor C to a point for correction (FIG. 16B illustrates a situation of moving the cursor C against a point $P_{7(Before)}$ for correction along the direction of arrow AR1). Then, the coordinates of the moving cursor C are stored sequentially (step 153: S153)

Here, as shown in FIG. 17, it is executed to judge whether there is the point (e.g. $P_{7(Before)}$) forming the defect preference area 100 for correction inside a circle with radius $r_2$ or not (step 154: S154). When it is judged at step 154: S154 that there is no point in question (NO at step 154: S154), then the process is ended. Note that the size of radius $r_2$ may be altered to an appropriate value. As shown in FIG. 17, concretely, it is executed to judge whether a circular cursor C contains the point $P_{7(Before)}$ or not.

When there is a point forming the defect preference area 100 in the cursor C (YES at step 154: S154), it is executed to calculate a distance for moving such a point (step 155: S155). In detail, it is performed to shift the point $P_{7(Before)}$ $(x_{01}, y_{01})$ of FIG. 17 from a center O $(x_{00}, y_{00})$ of the cursor C by a predetermined distance (radius $r_2$) in the moving direction (AR1 direction). Concretely, the coordinates of a destination: $P_{7(After)}$ $(x_{02}, y_{02})$ of $P_{7(Before)}$ is calculated in the form of $x_{02}=x_{00}+\Delta x_2$ and $y_{02}=y_{00}+\Delta y_2$. At last, the destination point $(P_{7(After)})$ is displayed again (step 156: S156) and the process is ended. This process will be repeated by given number of times.

Due to the move function, for instance, the point $P_{7(Before)}$ shown in FIG. 16B is moved to the point $P_{7(After)}$. Repeated performance of this operation allows a defect P to be surrounded more precisely.

[Noise Canceling Function]

Next, the noise canceling function will be described with reference to FIGS. 18 and 19.

The noise canceling function is one function provided to reinforce e.g. step 8: S8 of FIG. 2. For instance, in the process shown in step 7: S7 of FIG. 2, the above function is characterized by deleting an accidentally-clicked point $P_{11}$ automatically and further connecting a point $P_{10}$ with a point $P_1$ to draft a defect preference area 100 deleting an unnecessary place, as shown in FIG. 18. Referring to FIG. 19, we describe the function below.

When the inspection staff draws the defect preference area 100 under condition that the operations at steps 7 and 8 with the noise canceling function are started, it is executed to store the coordinates forming the defect preference area 100 that the staff is drawing at regular time intervals, automatically and sequentially (step 191: S191). Here, it may be constructed so that the inspection staff memorizes the defect mode (step 192: S192).

Next, by the inspection staff, it is executed to select an optional point from the coordinates drawn and stored at step 191: S191, as a starting point (step 193: S193). Suppose below, for instance, the point $P_1$ is selected in FIG. 18. Note that although the inspection staff selects the starting point, it may be modified so that the system can determine the starting point automatically.

Next, it is executed to determine a point closest to the selected starting point, establishing one line segment (step 194: S194). This process may be carried out automatically. Alternatively, the inspection staff may the next selective point following the starting point manually. The process at step 194: S194 is repeated until the point at step 194: S194 accords with the point (starting point) at step 192: S192 (step 195: S195). If the judgment at step 195: S195 is NO, it is executed to draw a new defect preference area 100 formed by the selected points only (step 1,96: S196) and the process is ended.

Figure 18:
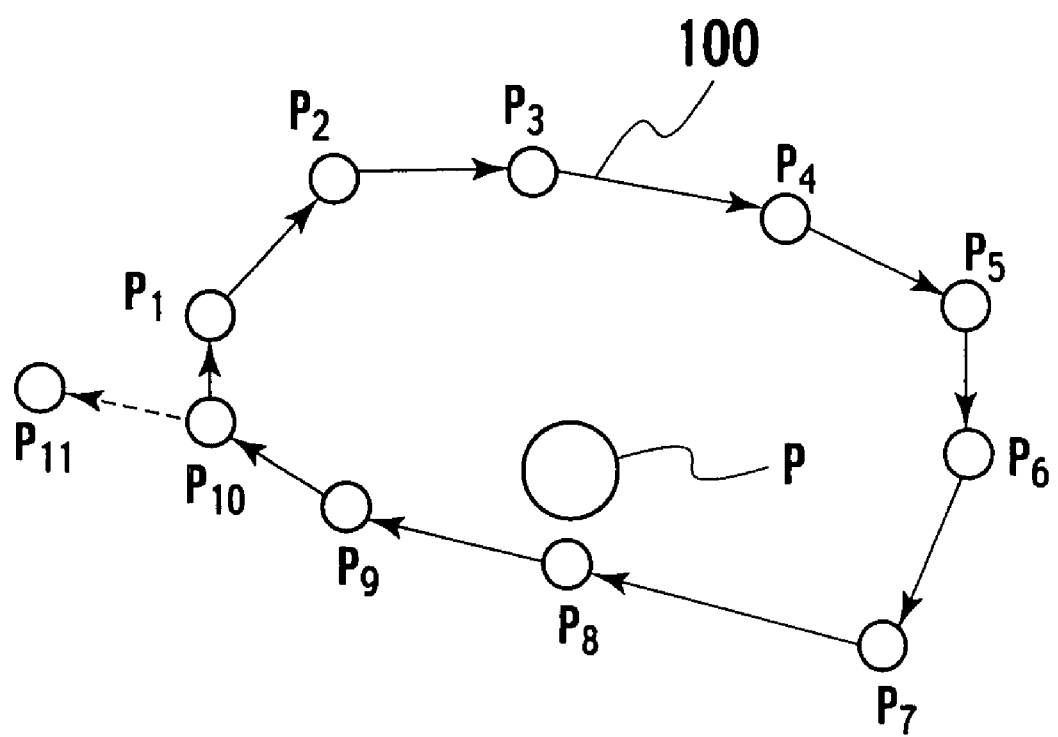
FIG. 18 is an explanatory view to explain a noise canceling function.
Figure 19:
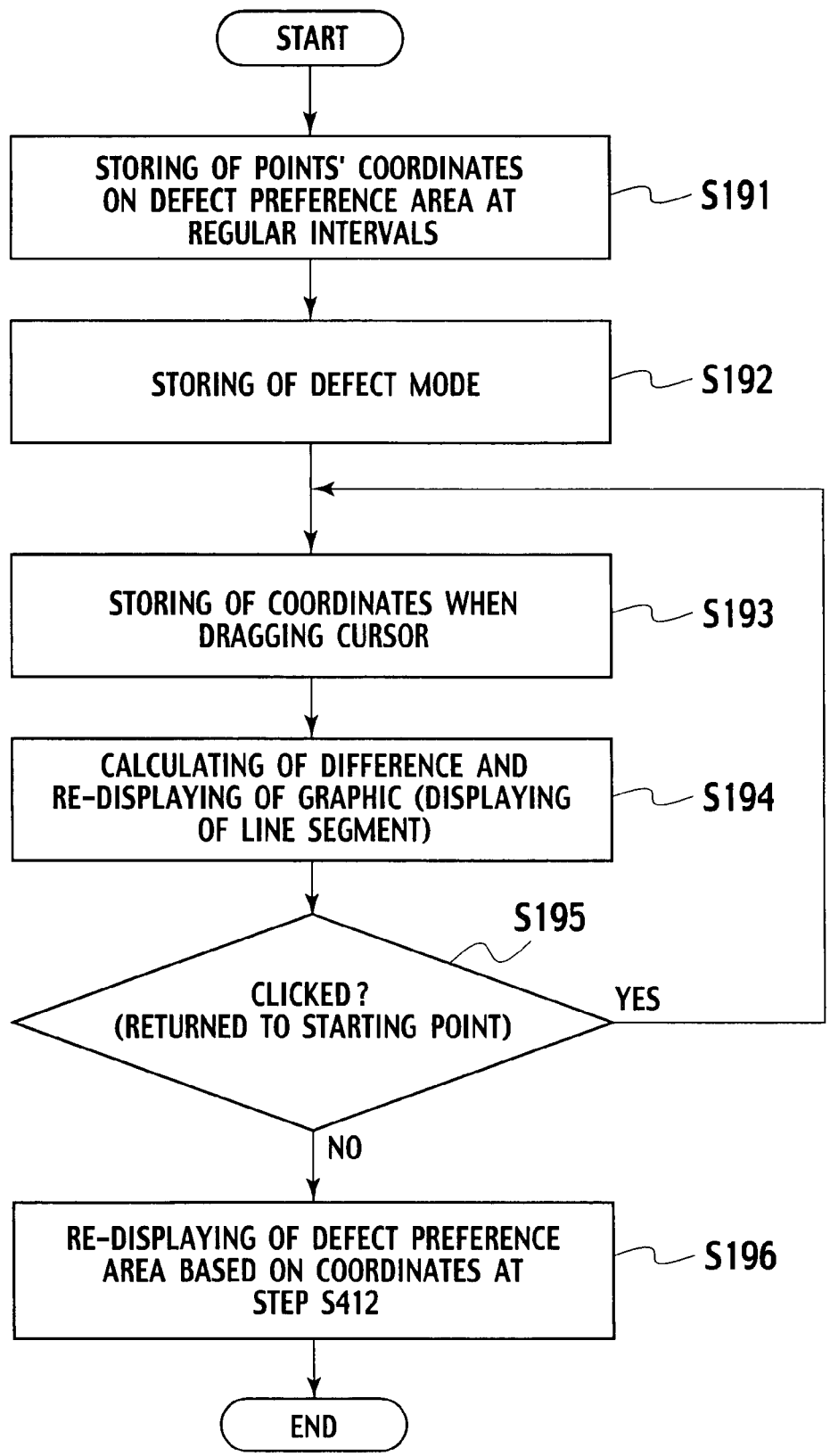
FIG. 19 is a flow chart to explain the noise canceling function.

In the example shown in FIG. 18, the points for the defect preference area 100 that the inspection staff drew at first comprise points $P_1$ to $P_{11}$, while the points for the new defect preference area 100 established with the noise canceling function automatically comprise the points $P_1$ to $P_{10}$. In this way, if the noise canceling function is employed, then it becomes possible to exclude a possibility of drafting a distorted defect preference area (polygon) and also possible to lighten a noise removal work.

[Line Defect Plotting Function]

Next, we explain a line defect plotting function for plotting a line defect precisely with reference to FIGS. 20 to 22B. The "line defect" means an aggregation of point defects continuing in a straight line transversely or vertically on a display device to be inspected.

Figure 20:
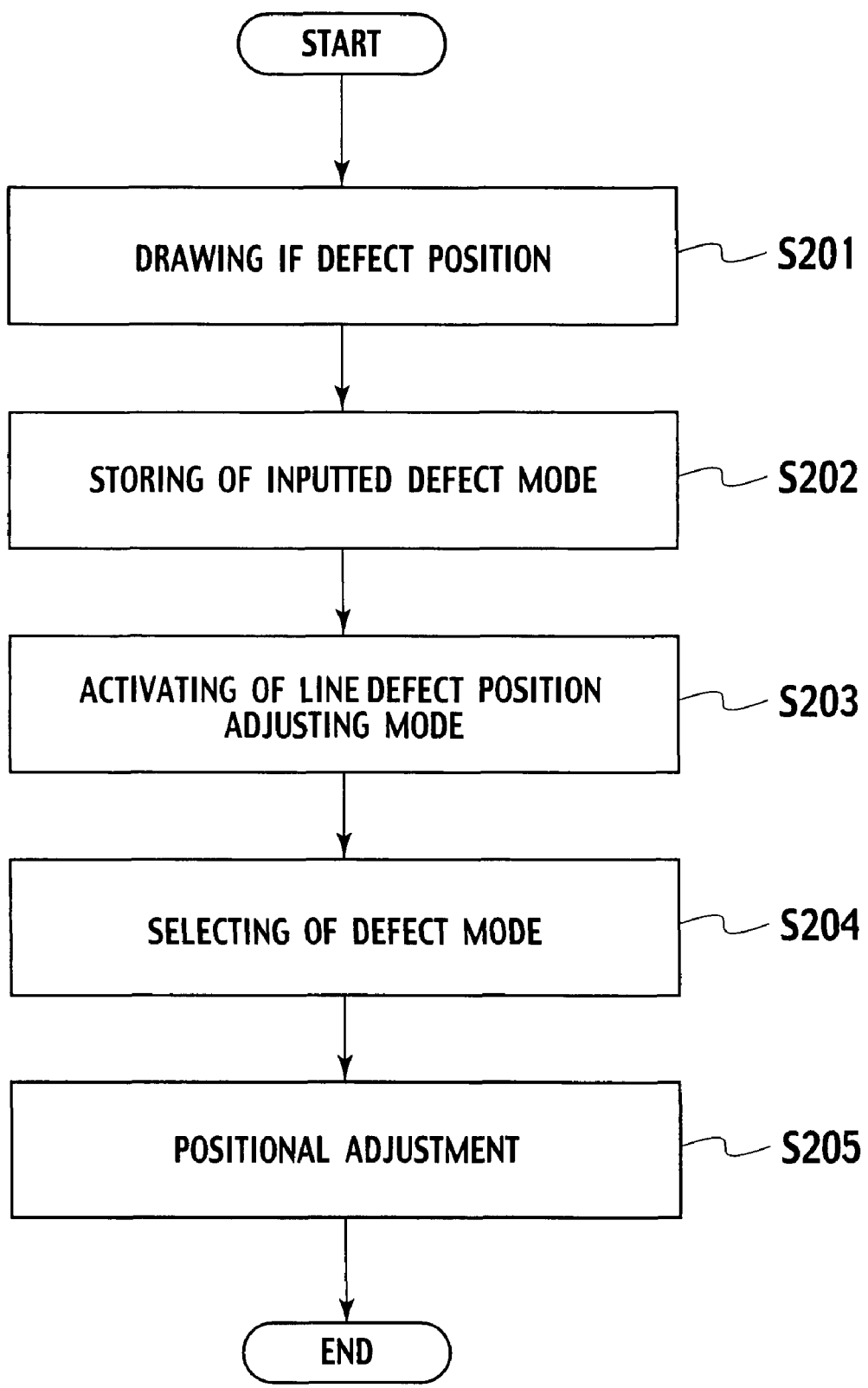
FIG. 20 is a flow chart to explain a line-defect plotting function of the present invention.

Similarly to the addressing function (point defect plotting function) of FIG. 12, the line defect plotting function is called out after a process of drawing a defect place (step 201: S201) and a sequent process of inputting the defect mode (step 202: S202), as shown in FIG. 20 (step 203: S203). Then, after the line defect plotting function is called out, the defect mode is selected (step 204: S204) and successively, the positional adjustment of defect is started (step 205: S205). The positional adjustment of defect (step 205: S205) as a feature of this function will be described in detail below.

Figure 21:
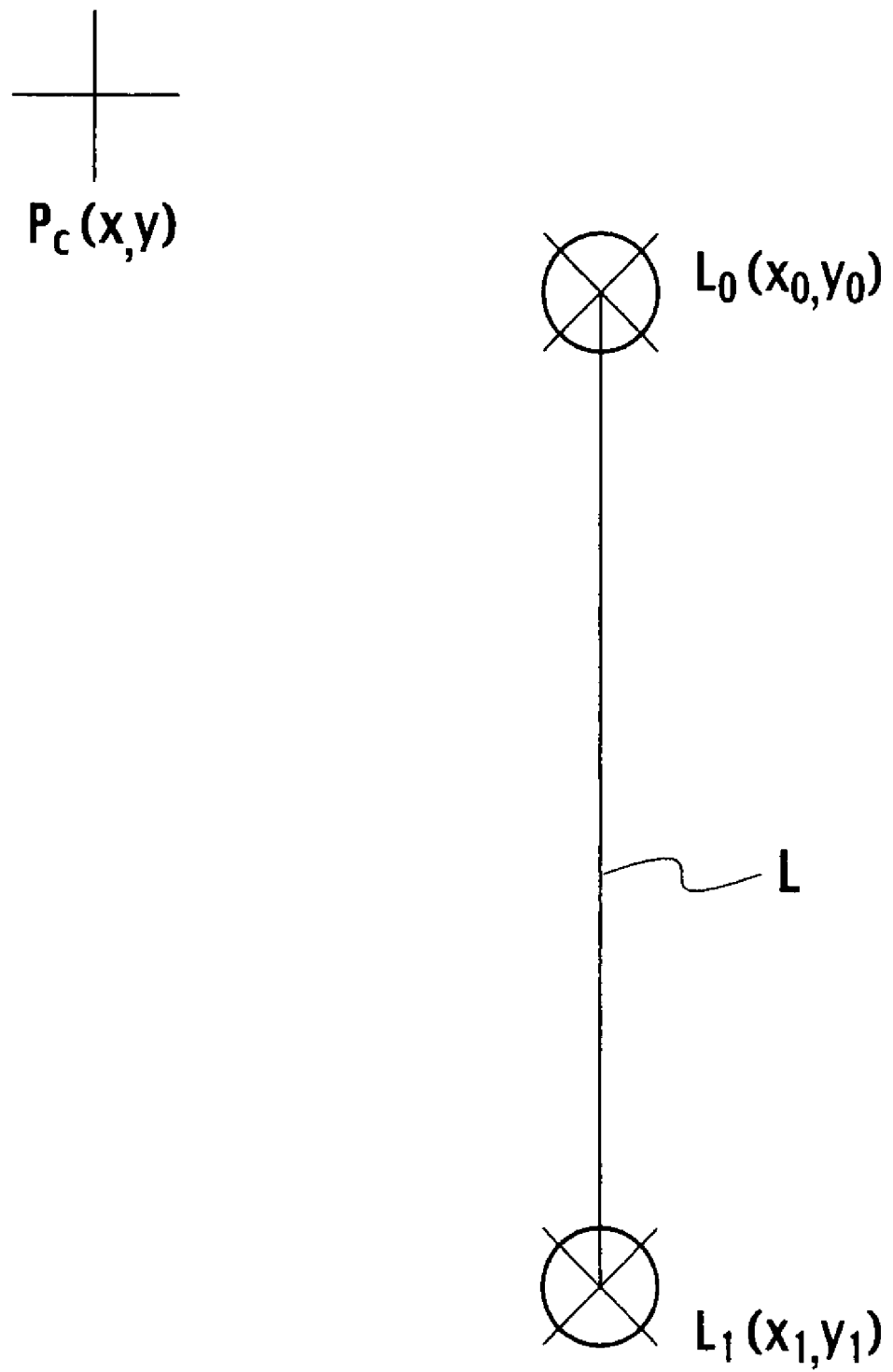
FIG. 21 is an explanatory view to explain the line-defect plotting function.
Figure 22A:
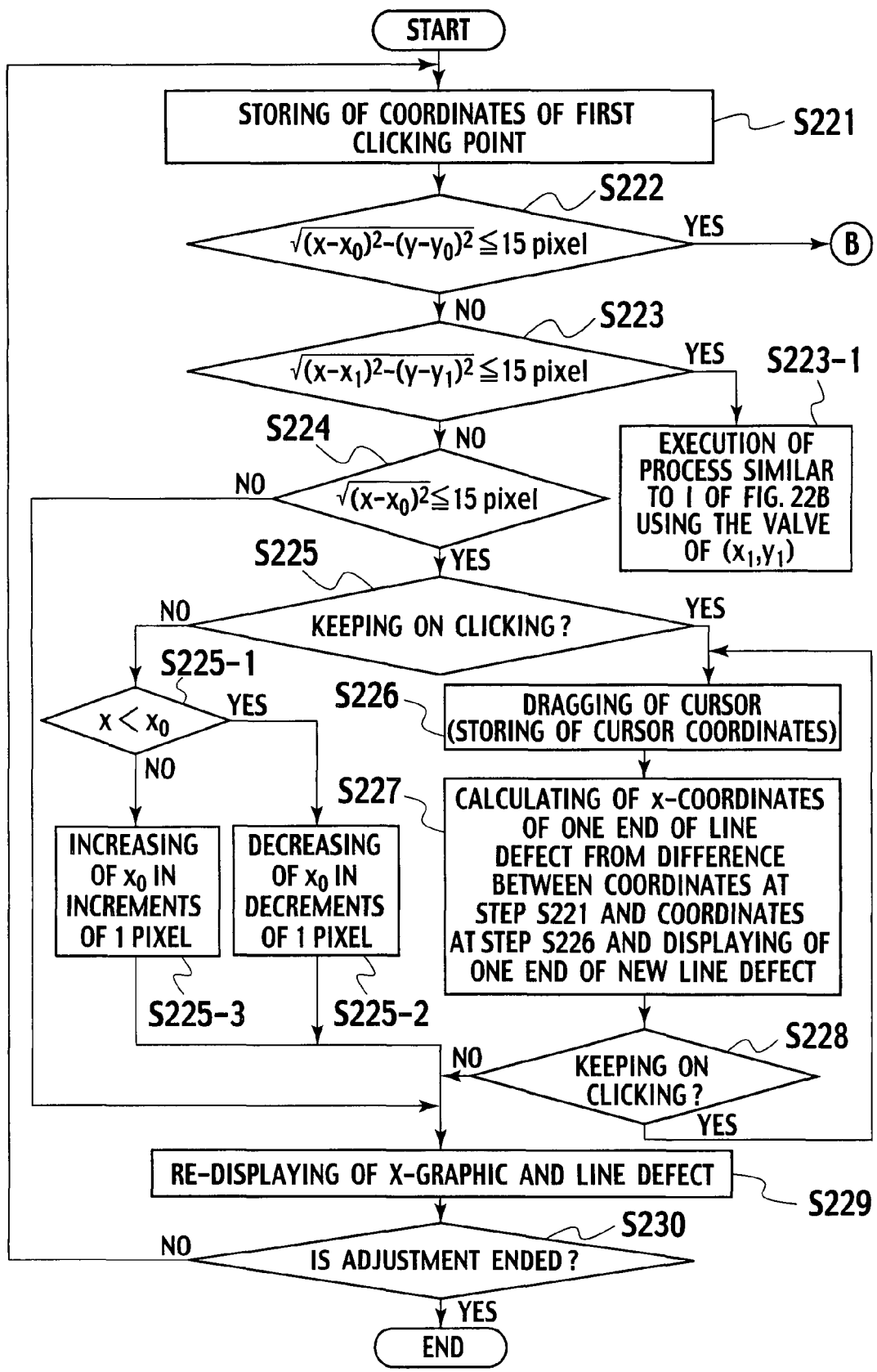
FIG. 22A is a flow chart of a position adjusting process of the line-defect plotting function.
Figure 22B:
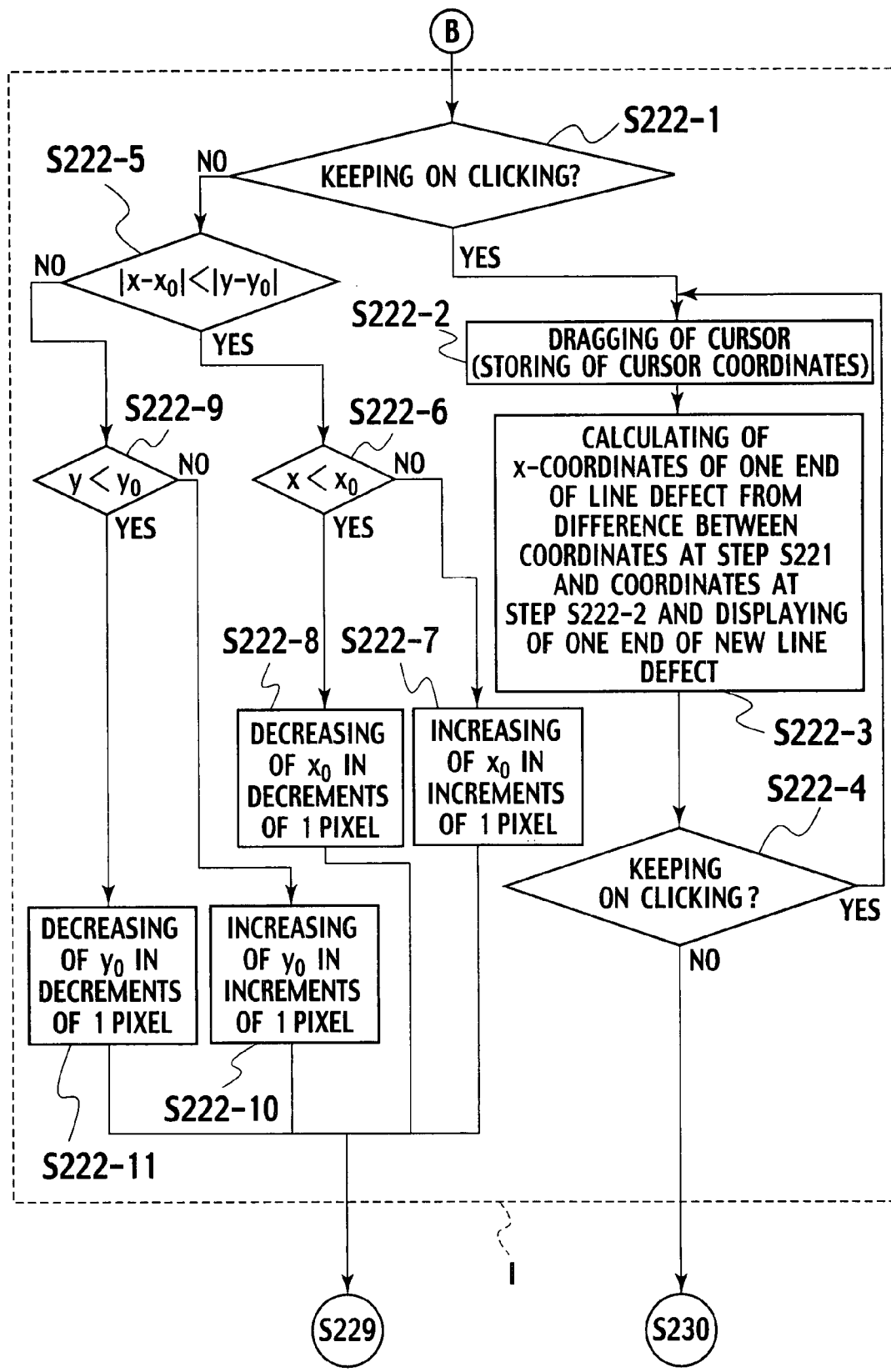
FIG. 22B is a flow chart of a position adjusting process of the line-defect plotting function.

Suppose below, a situation shown in FIG. 21 where a line defect L [a line segment connecting one point $L_0(x_0, y_0)$ with another point $L_1(x_1, y_1)$] is plotted by a cursor $P_c(x, y)$ precisely. However, it is noted that a line defect extending in the direction of X-axis could be coped by replacing a treatment for X-axis with the same for Y-axis in the following description.

When the positional adjustment of defect is started (step 205: S205), it is executed to store the coordinates of a first point that the inspection staff has clicked in order to designate the coordinates of the line defect L (step 221: S221). Next, it is executed to judge whether a distance between the coordinates of the cursor acquired at step 221: S221 and the end point $L_0$ of the line defect L is less than a predetermined value or not. If the distance between the cursor and the one end exceeds the predetermined value (NO at step: S222), it is executed to judge whether a distance between the cursor and the other end $L_1$ of the line defect L is less than the predetermined value or not. Although the example shown in FIG. 22 adopts 15 pixels as the predetermined value at steps 222: S222 and 223: S223, the present invention is not limited to this value only.

If the distance between the cursor and the other end exceeds the predetermined value (NO at step 233: S233), it is executed to judge whether a distance between the cursor $P_c$ and the end point $L_0$ of the line defect in the direction of X-axis is less than the predetermined value or not (step 224: S224). If the distance in the direction of X-axis is less than the predetermined value (YES at step 224: S 224), then it is executed to judge whether the inspection staff keeps on clicking or not (step 225: S225). Note that when the judgment at step 224: S224 is NO, the process goes to a process at step 228: S228 described later.

If the inspection staff keeps on clicking (YES at step 225: S225), it is executed to sequentially store the coordinates of the cursor P at that time since the inspection staff is dragging the cursor (step 226: S226). Then, it is executed to calculate a difference in the x-component between the cursor C at steps 221: S221, 226: S226 and the one end point 143. By adding/subtracting the so-calculated difference to and from the x-component of the end point L0, additionally, it is executed to determine an x-component of the end point L0 of a new line defect L and further display the line defect L on the basis of new coordinates (step 227: S227). Next, the presence/absence of an inspection staff's inputting is judged (step 228: S228). If the inspection staff continues to move the cursor (keep on dragging), then it is executed to send the process back to step 226: S226. While, if the staff does not move the cursor, it is executed to display a graphic representing a starting point (end point) on both ends L and L1 of the line defect L, for instance, marks X in FIG. 21 (which will be referred to as "X-graphic") (step 229: S229) and further executed to judge whether the adjustment is completed or not (step 230: 230). Note that if the adjustment is not completed (NO at step 230: 230), it is executed to send the process back to step: S211 where the above-mentioned processes are repeated.

When it is judged that the inspection staff does not continue to click at step 225: S225 (NO at step 225: S225), then it is executed to judge whether an x-component x of the cursor P is smaller than an x-component XO of the end point L0 of the line defect L or not (step 225-I: S225-1). If the x-component of the cursor P is smaller than the x-component X of the end point L0 (YES at step 225-1: S225-1), the value XO is decreased in decrements of 1 pixel (step 225-2: S225-2) and the process goes to step S229. On the other hand, if the x-component of the cursor P is larger than the x-component x0 of the end point Lo (NO at step 225-1: S225-I), the value x0 is increased in increments of I pixel (step 225-3: S225-3) and thereafter, the process goes to step S229.

On the other hand, if the distance between the cursor P and the end point L0 of the line defect L is less than the predetermined value (YES at step 222: S222), it is first executed to judge whether the inspection staff keeps on clicking or not (step 222-1: S222-i). If it is judged that the inspection staff keeps on clicking (YES at step 222-i: S222-i), it is executed to sequentially store the coordinates of the cursor P since the inspection staff moves (drags) the cursor P (step 222-2: S222-2). Here, it is executed to calculate a difference between the coordinates of the cursor P stored at step 221: S221 and the coordinates of the cursor P stored at step 222-2: S222-2. Additionally, it is executed to calculate new coordinates of L0 of the line defect L by the so-obtained difference and further executed to display the line defect L on the basis of the new coordinates (step 222-3: S222-3). Next, it is executed to judge whether the inspection staff continues to click or not (step 222-4: S222-4). If it is judged that the staff keeps on clicking, it is executed to send the process back to step 222-2: S222-2 where the above-mentioned processes are repeated. In case of no clicking, the process goes to step 230: S230.

If it is judged that the inspection staff does not click at step 222-1: S222-1 (No at step 222-1: S222-1), it is executed to judge the magnitude relation between a distance in the direction of X-axis between the cursor P and the end point L and another distance in the direction of Y-axis between the cursor P and the end point L0 (step 222-5: S222-5). When the distance in the direction of Y-axis is larger (YES at step 222-5: S222-5), it is executed to judge the magnitude relation between the x-component of the cursor P and the x-component of the end point L0 (step 222-6: S222-6). Here, when the x-component of the cursor PC is larger (NO at step 222-6: S222-6), the x-component x0 of the end point L0 is increased in increments of 1 pixel (step 222-7: S222-7) and thereafter, the process goes to step 228: S229. On the other hand, when the x-component of the cursor P is smaller (NO at step S222-6), the x-component x0 of the end point L0 is decreased in decrements of 1 pixel (step 222-8: S222-8) and thereafter, the process goes to step S238.

Further, if the distance in the direction of Y-axis is smaller than the distance in the direction of X-axis (No at step 222-5: S222-5), it is executed to judge the magnitude relation between the y-component of the cursor PC and the y-component of end point L0 (step 222-9: S222-9). 1-lere, if the y-component of the cursor PC is larger (NO at step 222-6: S222-6), the value of the y-component yo is increased in increments of 1 pixel (step 222-10: S222-10) and thereafter, the process goes to step 229: S229. On the other hand, when the y-component of the cursor PC is smaller (YES at step 222-9: S222-9), the value of the y-component yo of the end point L0 is decreased in decrements of I pixel (step 222-il: 5222-li) and thereafter, the process goes to step S228.

Note that if it is judged at step 223: S223 that the distance between the cursor $P_c$ and the other end L, of the line defect L is more than the predetermined value (YES at step 223: S223), an operation similar to steps 222-1: S2222 and the following steps (process group I of FIG. 22B) is applied to the coordinates $x_1$, $y_1$.

Note that the above-mentioned addressing function, the shift function, the move function, the noise canceling function and the point-defect plotting function are added as e.g. one function of the defect information identification controlling part 13 of the defect inspection apparatus 1.

3$^{rd}$. Embodiment

Figure 23:
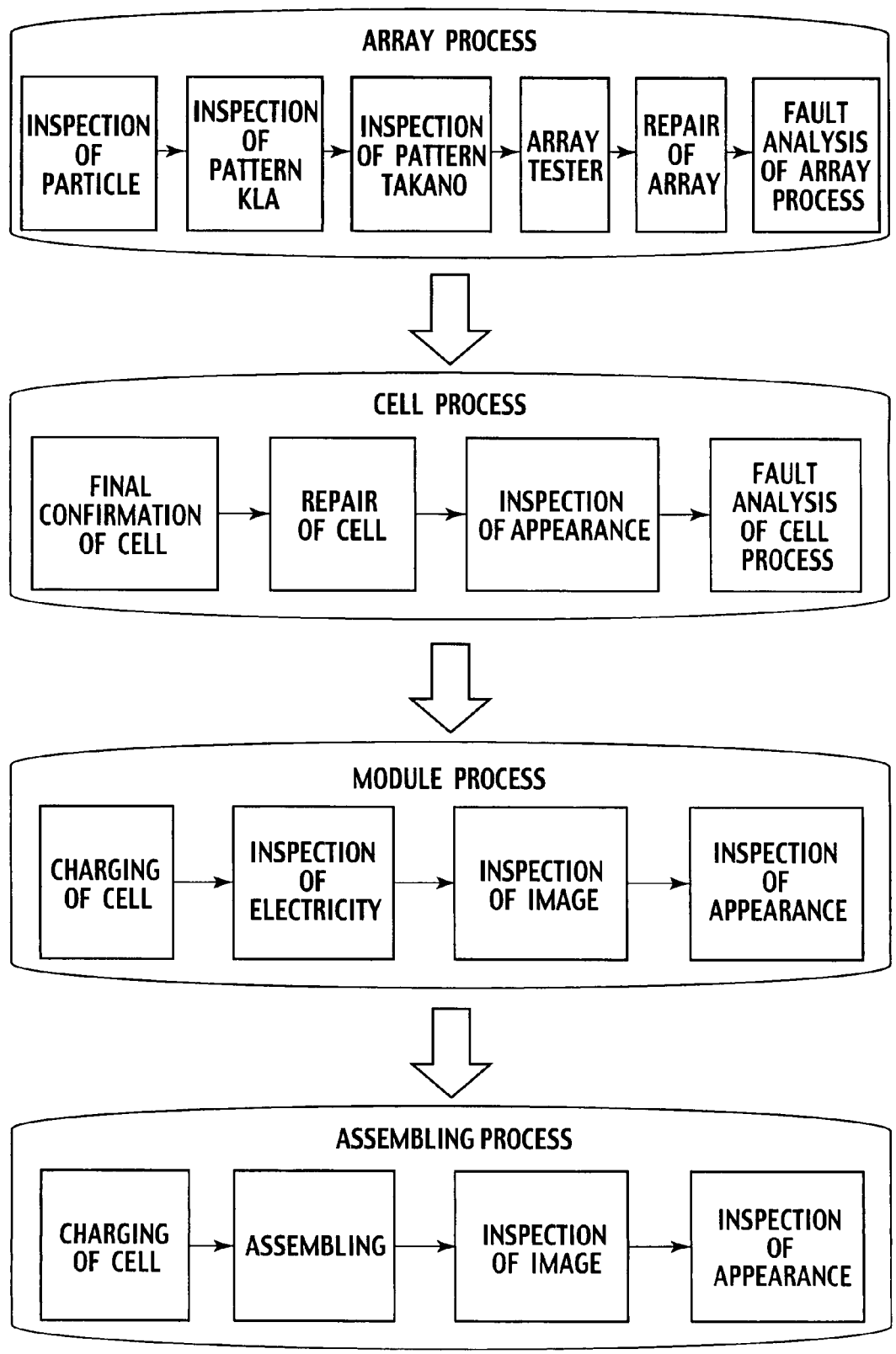
FIG. 23 is an explanatory view to explain a manufacturing process of display devices to which the present invention is applicable.

FIG. 23 is a view showing the production process in manufacturing a display device, for example, liquid crystal device. The production process comprises an array process, a cell process and a module process. Although it is assumed in common with the first embodiment and the second embodiment that the defect inspection apparatus 1 is utilized to analyze defects in the cell process, the defect inspection apparatus of this embodiment is also applicable to the module process. Additionally, if installing the above-mentioned functions in an end product, such as note-type personal computer, the present invention could be embodied as a substitute article of the defect inspection apparatus 1. Thus, the present invention may be embodied in an assembling process as well.

In detail, the present invention is also applicable to an image inspecting step in either the module process or the assembling process.

INDUSTRIAL APPLICABILITY

According to the present invention mentioned above, it is possible to provide display-device instruction apparatus and method that allow results of the screen inspection in the manufacturing process for display devices to be stocked for storage with ease and that further enable the stored result of screen inspection to be analyzed or outputted as occasion demands, thereby improving both production efficiency and quality of the display devices.

The invention claimed is:

1. A display-device inspection method for inspecting a display device on viewing an image displayed on a screen of the display device, comprising:
a position nominating step of allowing identification position nominating means to nominate an attention area in the screen thereby executing an identification of the attention area;
an extracting step of allowing attention area information extracting means to extract both positional information and shape information related to the attention area;
a storing step of allowing attention area information storing means to classify and store the positional information and the shape information on a basis of a predetermined standard of classification;
an outputting step of allowing analysis result outputting means to output inspection result information constructed by analyzing contents stored in the attention area information storing means; and
a correcting step of correcting the positional information and the shape information related to the attention area extracted at the position nominating step or the extracting step,
wherein the correcting step further includes an addressing step, comprising:
a storing step of storing coordinates of a point inputted by using the identification position nominating means, as an initial value;
a judging step of judging whether a distance between the initial value stored at the storing step and coordinates of a point forming the attention area as an object to be corrected is less than a predetermined value or not;
if the distance at the judging step is less than the predetermined value, a first moving step of moving the coordinates of the point forming the attention area in a direction of X-axis or Y-axis by a predetermined amount;
if the distance at the judging step exceeds the predetermined value, a second storing step of storing coordinates of a point successively inputted from the identification position nominating means;
a calculating step of calculating a difference between the coordinates stored at the second storing step and the coordinates of the initial value;
a second moving step of moving the coordinates of the initial value by the difference calculated at the calculating step; and
a repeating step of repeating the second storing step so long as values at the second storing step continue to be renewed.

2. A display-device inspection method for inspecting a display device on viewing an image displayed on a screen of the display device, comprising:
a position nominating step of allowing identification position nominating means to nominate an attention area in the screen thereby executing an identification of the attention area;
an extracting step of allowing attention area information extracting means to extract both positional information and shape information related to the attention area;
a storing step of allowing attention area information storing means to classify and store the positional information and the shape information on a basis of a predetermined standard of classification;
an outputting step of allowing analysis result outputting means to output inspection result information constructed by analyzing contents stored in the attention area information storing means; and
a correcting step of correcting the positional information and the shape information related to the attention area extracted at the position nominating step or the extracting step,
wherein the correcting step further includes a shift mode function, comprising:
a first storing step of storing a first point inputted by using the identification position nominating means, as an initial value;
a second storing step of sequentially storing coordinates of a point inputted in succession to the input of the initial value;
a calculating step of calculating a difference between the coordinates stored at the second storing step and the initial value stored at the first storing means step; and
a moving step of moving the attention area by the difference calculated at the calculating step.

3. A display-device inspection method for inspecting a display device on viewing an image displayed on a screen of the display device, comprising:
a position nominating step of allowing identification position nominating means to nominate an attention area in the screen thereby executing an identification of the attention area;
an extracting step of allowing attention area information extracting means to extract both positional information and shape information related to the attention area;
a storing step of allowing attention area information storing means to classify and store the positional information and the shape information on a basis of a predetermined standard of classification;
an outputting step of allowing analysis result outputting means to output inspection result information constructed by analyzing contents stored in the attention area information storing means; and
a correcting step of correcting the positional information and the shape information related to the attention area extracted at the position nominating step or the extracting step,
wherein the correcting step further includes a move step comprising:

a selecting step of selecting both positional information and shape information related to an attention area desired to be corrected;

a displaying step of displaying coordinates of a point forming the positional information and the shape information on selection;

a storing step of storing coordinates of the identification nominating means sequentially;

if the coordinates displayed at the displaying step are present within a predetermined distance from the center of the coordinates of the identification nominating means obtained at the storing step, a moving step of moving the coordinates of the point in a moving direction of the identification nominating means by the determined distance; and a re-displaying step of re-displaying the point after being moved.

4. A display-device inspection method for inspecting a display device on viewing an image displayed on a screen of the display device, comprising:

a position nominating step of allowing identification position nominating means to nominate an attention area in the screen thereby executing an identification of the attention area;

an extracting step of allowing attention area information extracting means to extract both positional information and shape information related to the attention area;

a storing step of allowing attention area information storing means to classify and store the positional information and the shape information on a basis of a predetermined standard of classification;

an outputting step of allowing analysis result outputting means to output inspection result information constructed by analyzing contents stored in the attention area information storing means; and a correcting step of correcting the positional information and the shape information related to the attention area extracted at the position nominating step or the extracting step, wherein the correcting step further includes, at the position nominating step, a noise canceling step comprising:

a storing step of storing coordinates of the attention area when the identification nominating means nominates the attention area, in the form of sequence of points on the basis of an original point;

a first additional step of adding an adjacent point closest to the original point to the sequence of points;

a second additional step of adding an adjacent point closest to the adjacent point to the sequence of points;

a repeating step of repeating the second additional step up to a last point stored at the storing step finally; and a displaying step of displaying a polygon formed by points stored in the sequence of points.

* * * * *